United States Patent
Tran et al.

(10) Patent No.: US 8,951,793 B2
(45) Date of Patent: Feb. 10, 2015

(54) METHOD OF MAKING AN ISOLATED POPULATION OF FOXP3+ REGULATORY T CELLS

(75) Inventors: Dat Tran, Gaithersburg, MD (US); Ethan M. Shevach, Rockville, MD (US)

(73) Assignee: The United States of America, as represented by The Secretary, Department of Health and Human Services, Washington, DC (US)

( * ) Notice: Subject to any disclaimer, the term of this patent is extended or adjusted under 35 U.S.C. 154(b) by 788 days.

(21) Appl. No.: 13/060,043

(22) PCT Filed: Aug. 21, 2009

(86) PCT No.: PCT/US2009/054631
§ 371 (c)(1),
(2), (4) Date: May 10, 2011

(87) PCT Pub. No.: WO2010/022341
PCT Pub. Date: Feb. 25, 2010

(65) Prior Publication Data
US 2011/0300119 A1    Dec. 8, 2011

Related U.S. Application Data

(60) Provisional application No. 61/090,788, filed on Aug. 21, 2008, provisional application No. 61/155,430, filed on Feb. 25, 2009, provisional application No. 61/185,933, filed on Jun. 10, 2009.

(51) Int. Cl.
*C12N 5/07* (2010.01)
*C12N 5/00* (2006.01)
(Continued)

(52) U.S. Cl.
CPC ......... *C12N 5/0636* (2013.01); *A61K 2035/122* (2013.01); *C12N 2501/15* (2013.01); *C12N 2501/23* (2013.01); *C12N 2501/51* (2013.01); *C12N 2501/515* (2013.01)
USPC ....... 435/372.3; 435/7.2; 435/7.24; 435/7.29; 435/174; 435/325; 435/343.2; 435/383; 424/93.7; 436/518; 530/388.75

(58) Field of Classification Search
CPC .......... C12N 5/00; C12N 5/06; C12N 5/0636; C12N 5/0637; C12N 11/00; C12Q 1/02; G01N 2446/00; G01N 2469/00; G01N 2469/10; G01N 33/00; G01N 33/53; G01N 33/543; A01N 63/00
See application file for complete search history.

(56) References Cited

U.S. PATENT DOCUMENTS 8,053,197 B2 *  11/2011   Vandenbark et al. .......... 435/7.1
8,053,235 B2 *  11/2011   Buckner et al. ............ 435/372.3
(Continued)

FOREIGN PATENT DOCUMENTS

EP          2113561 A1      11/2009

OTHER PUBLICATIONS

Gandhi, R., et al., "Cutting Edge: Immature human dendritic cells express latency-associated peptide and inhibit T cell activation in a TGF-beta-dependent manner," J Immunol., Apr. 1, 2007; 178(7):4017-21.
(Continued)

*Primary Examiner* — David M Naff
(74) *Attorney, Agent, or Firm* — Sheridan Ross P.C.

(57) ABSTRACT

Disclosed are methods of isolating and using a population of FOXP3+ regulatory T cells in a variety of preventative and therapeutic approaches to autoimmune diseases, graft-versus-host disease and transplant rejection.

17 Claims, 12 Drawing Sheets

Figure 1:
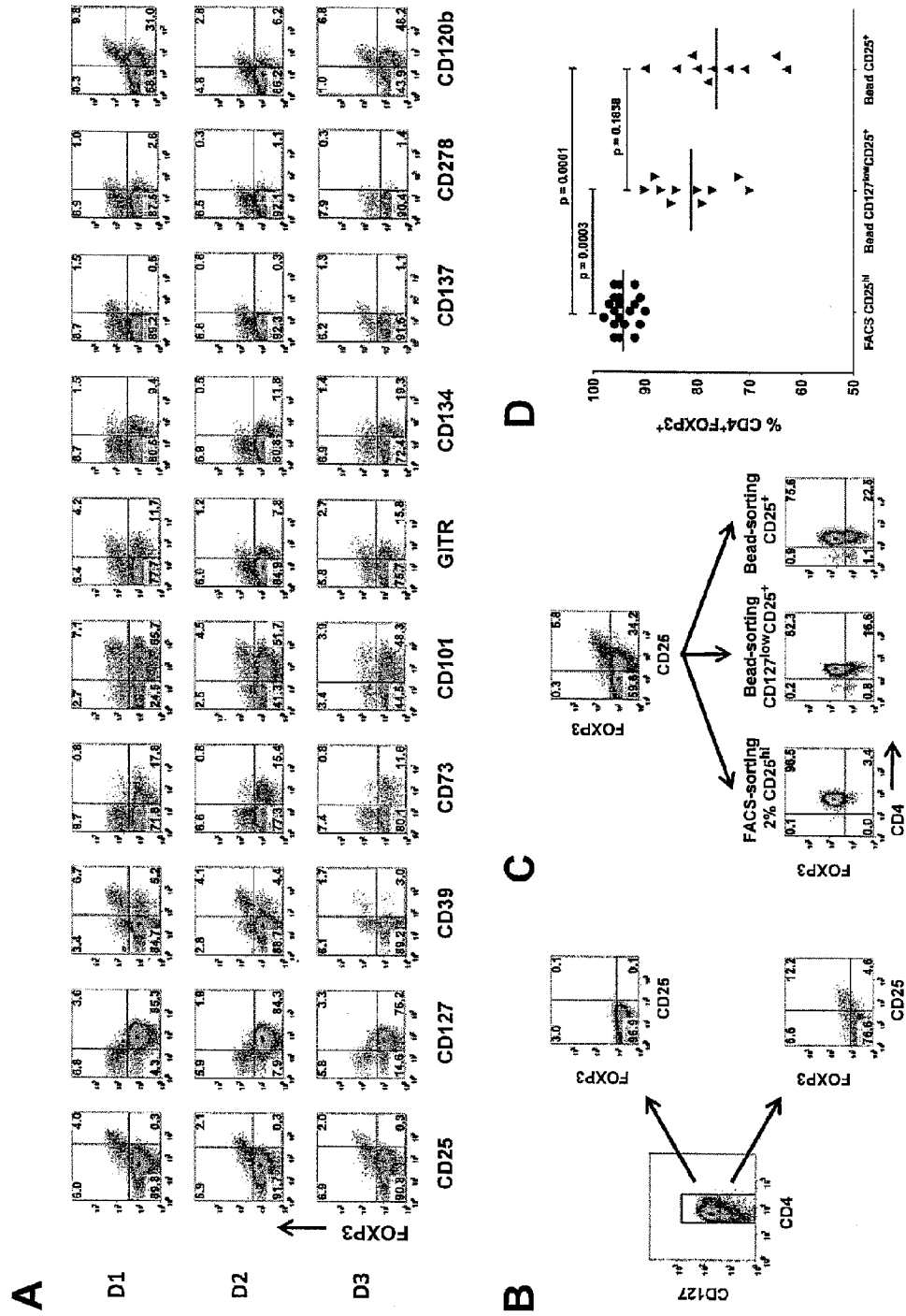

(51) Int. Cl.
| | |
|---|---|
| C12N 5/0783 | (2010.01) |
| C12N 11/00 | (2006.01) |
| C12Q 1/02 | (2006.01) |
| G01N 33/53 | (2006.01) |
| G01N 33/00 | (2006.01) |
| G01N 33/543 | (2006.01) |
| A01N 63/00 | (2006.01) |
| C07K 16/18 | (2006.01) |
| A61K 35/12 | (2006.01) |

(56) References Cited

U.S. PATENT DOCUMENTS

| | | | | |
|---|---|---|---|---|
| 8,129,126 | B2 * | 3/2012 | Thiel et al. | 435/7.1 |
| 8,415,154 | B2 * | 4/2013 | Noelle | 435/377 |
| 8,563,308 | B2 * | 10/2013 | Steinman et al. | 435/372.3 |
| 2005/0118655 | A1 * | 6/2005 | Weinstock et al. | 435/7.22 |
| 2006/0062763 | A1 * | 3/2006 | Godfrey et al. | 424/93.1 |
| 2008/0175830 | A1 | 7/2008 | Steinman et al. | |

OTHER PUBLICATIONS

Hoechst, Bastian, et al., "A New Population of Myeloid-Derived Suppressor Cells in Hepatocellular Carcinoma Patients Induces CD4+CD25+Foxp3+ T Cells" Gastroenterology, 2008, vol. 135, No. 1, pp. 234-243.

Hougardy, Jean-Michel, et al., "In vitro expansion of CD4+CD25$^{high}$FOXP3+CD127$^{low/-}$ regulatory T cells from peripheral blood lymphocytes of healthy *Mycobacterium tuberculosis*-infected humans" Microbes and Infection, 2007, vol. 9, pp. 1325-1332.

Garaczi, E., et al., "Glycoprotein A repetition predominant: a novel marker of human CD4+CD25high+ regulatory T cells", Journal of Investigative Dermatology, Nature Publishing Group, GB, vol. 124, No. 4 Suppl. S, Apr. 1, 2005 p. A117, XP008080090, ISSN: 0022-202X, Abstract.

Hoffmann, Petra, et al., "Only the CD45RA+ subpopulation of CD4+CD25$^{high}$ T cells gives rise to homogeneous regulatory T-cell lines upon in vitro expansion" Blood, Dec. 15, 2006, vol. 108, No. 13, pp. 4260-4267.

Tran, Dat, et al., "T.I06. Selective Expression of Latency Associated Peptide (LAP) and IL-1 Receptor Type I/II (CD121a/CD121b) on Activated Human FOXP3+ Regulatory T Cells Allows for Their Purification from Expansion Cultures for Potential Immunotherapy," Clinical Immunology, Academic Press, US, vol. 131, Jan. 1, 2009, pp. S81-S82, XP026084632 ISSN: 1521-6616, Abstract.

Tran, Dat, et al., "Selective expression of latency-associated peptide (LAP) and IL-1 receptor type I/II(CD121a/CD121b) on activated human FOXP3+ regulatory T cells allows for their purification from expansion cultures," Blood, May 21, 2009, vol. 113, No. 21, pp. 5125-5133.

Tran, Dat, et al., GARP (LRRC32) is essential for the surface expression of latent TGF-β on platelets and activated FOXP3+ regulatory T cells, Proc Natl Acad Sci U S A. Aug. 11, 2009;106(32):13445-50. Epub Jul. 27, 2009.

Tran, Dat Q., et al., Therapeutic potential of FOXP3+ regulatory T cells and their interactions with dendritic cells; Human Immunology, 2009, 70:294-299.

Wang, Rui, et al., "Identification of a Regulatory T Cell Specific Cell Surface Molecule that Mediates Suppressive Signals and Induces Foxp3 Expression," PLosONE, Jul. 2008, vol. 3, Issue 7, pp. 1-9.

International Search Report, dated Dec. 1, 2009, in PCT/2009/054631.

International Patent Report on Patentability, dated Mar. 11, 2011, in PCT/2009/054631.

* cited by examiner

METHOD OF MAKING AN ISOLATED POPULATION OF FOXP3+ REGULATORY T CELLS

CROSS REFERENCE TO RELATED APPLICATIONS

This application is a national stage application under 35 U.S.C. 371 of PCT Application No. PCT/US2009/054631 having an international filing date of 21 Aug. 2009, which designated the United States, which PCT application claimed the benefit of U.S. Provisional Application Nos. 61/090,788 filed Aug. 21, 2008; 61/155,430 filed Feb. 25, 2009; and 61/185,933 filed Jun. 10, 2009, the entire disclosure of each of which are hereby incorporated herein by reference.

FIELD OF THE INVENTION

The present invention generally relates to methods of purifying regulatory T cells and uses of these purified cells in the treatment of autoimmune disorders and transplant-related complications such as rejection and graft-versus-host disease.

BACKGROUND OF THE INVENTION

It is widely accepted that regulatory T cells (Tregs) are critical for the prevention of autoimmunity and maintenance of self-tolerance throughout the lifespan of a human being. A diminished frequency or dysfunction of Tregs has been reported in many human diseases, including systemic lupus erythematosus (SLE), rheumatoid arthritis, type 1 diabetes, multiple sclerosis (MS), aplastic anemia, idiopathic thrombocytopenic purpura, and graft-versus-host disease (GVHD), as well as transplant rejection. Due to questions surrounding the purity of the Tregs used in these studies, however, the role of Tregs in the pathogenesis of these human diseases remains unclear.

In contrast, the evidence is strong regarding the utility of Tregs for the treatment of autoimmunity in murine models. In murine studies, adoptive immunotherapy with Tregs has been shown to be effective in the prevention of experimental autoimmune encephalomyelitis (EAE), type 1 diabetes, SLE, autoimmune gastritis, inflammatory bowel disease (IBD), asthma, aplastic anemia, graft rejection, and GVHD.

Currently, enhancing graft acceptance and preventing GVHD are probably the most fruitful areas for the application of Treg immunotherapy in humans and a related condition that might greatly benefit from Treg immunotherapy is chronic GVHD (cGVHD). Approximately 30-50% of patients receiving allogeneic HSCT will develop cGVHD, which can be life threatening or can severely impair the patient's quality of life. With improvement in postgrafting immunosuppressive regimens, the number of individuals at risk for cGVHD is increasing. Treatment remains unsatisfactory and corticosteroids are still the mainstay of therapy. The pathophysiology and molecular mechanisms of this disease are still unclear. However, the loss of self-tolerance resulting in autoimmune manifestations is a major component.

Thus, a source of regulatory T cells for the treatment of autoimmunity and transplant rejection via adoptive immunotherapy in humans is urgently needed to advance the treatment of these prevalent but poorly treated diseases.

One aspect of Treg physiology that has not been considered is whether Tregs develop a normal T-cell receptor (TCR) repertoire after HSCT. Regulatory T cells develop in the thymus and their T-cell receptor (TCR) repertoire is shaped by interaction with thymic epithelial or dendritic cells. Tregs have been shown to express a diversified TCR repertoire similar to, but also distinct from, that of $CD4^+FOXP3^-$ conventional T cells. As the thymus microenvironment in patients who have received myeloablative treatment may be compromised, a factor contributing to the development of cGVHD is the development and selection of an abnormal or skewed TCR repertoire in Tregs, compared with conventional T cells. A loss of diversity of TCR expression in the donor's Treg population results in an inability of the Tregs to inhibit host-reactive effector cells, leading to the development of cGVHD.

The study of human Tregs and their use in therapy has been hampered by the inability to obtain sufficient numbers of these cells for cellular immunotherapy. There is a great need to overcome the inability to consistently achieve a highly purified $FOXP3^+$ Treg product after ex vivo expansion, secondary to the outgrowth of contaminating non-Tregs.

While a $CD4^+FOXP3^-$ population of more than 90% purity can be isolated by fluorescence-activated cell sorting (FACS) of the top 2-4% of $CD4^+$ T cells with low levels of CD127 and high levels of CD25 expression (CD127lowCD25hi) from peripheral blood, the percentage of $FOXP3^+$ T cells decreases to 75% after 1 week and to 50% after 2 weeks of in vitro expansion.

Different strategies have been developed to optimize the purity of Tregs. One method is the addition of rapamycin to the expansion cultures. This is based on the evidence that $FOXP3^-$ T cells are more susceptible to rapamycin-induced apoptosis than $FOXP3^+$ T cells. But it remains difficult to obtain populations of expanded $FOXP3^+$ with purity greater than 90% after 14 days of expansion using this technique and thus, the large variations in purity remain an issue.

The use of $CD4^+CD45RA^+CD25^{hi}$ Tregs as the starting population has also been advocated to improve the purity of Tregs during expansion. But it is difficult to isolate $CD45RA^+$ Tregs from adult peripheral blood, as the vast majority (>80%) of $FOXP3^+$ T cells are $CD45RA^-$ memory cells. Another concern is that contaminating $CD4^+CD45RA^+FOXP3^-$ cells are highly susceptible to conversion to $FOXP3^+$ non-Tregs by TGF-β in the culture medium used for expansion.

Thus, better methods for the isolation and expansion of Tregs that produce greater yields and purity, while maintaining regulatory T cell function, is needed before the treatment of autoimmunity and transplant rejection by adoptive immunotherapy will be viable.

SUMMARY OF THE INVENTION

The present invention provides methods of producing T regulatory cells (Tregs) suitable for use in adoptive immunotherapy and methods of using these cells.

One aspect of the invention is a method to repurify Tregs from $FOXP3^+$ non-Tregs and the $FOXP3^-$ contaminating effector T cells, using selective expression of surface markers unique to the Tregs.

In one embodiment, the disclosure provides methods of preparing lymphocytic cells by isolating human lymphocytes having CD4, CD25 and CD127low cell surface proteins, culturing the cells in a medium containing CD3, CD28, and IL-2 proteins and rapamycin for a suitable period of time, re-stimulating the cultures at least once with IL-2, CD3, and CD28; isolating T lymphocyte regulatory cells having cell surface markers of at least one of LAP, IL-1 receptor type I (CD121a), IL-1 receptor type II (CD121b) and GARP (LRRC32).

In one embodiment the method includes one of the additional steps of 1) selecting CD25+ cells or 2) depleting CD127+ cells, followed by the selection of CD25+ cells. One of these steps is then followed by the expansion and reisolation with LAP, CD121a, CD121b or GARP.)

In some embodiments, the cells are cultured for at least 12 days before restimulation.

In some embodiments, the T lymphocyte regulatory cells are isolated using an antibody specific for LAP.

In embodiments, the isolated T lymphocyte regulatory cells express Foxp3 protein.

In yet other embodiments, the method further comprises culturing the isolated T lymphocyte regulatory cells for a suitable period of time, such as at least 14 days.

In embodiments, the method further comprises isolating T lymphocyte regulatory cells using an antibody specific for an antigen selected from one or more of latency-associated peptide (LAP), IL-1 receptor type I (CD121a), IL-1 receptor type II (CD121b), GARP (LRRC32) and combinations thereof.

In one embodiment, the isolated T regulatory cells also express CD27, lymphocyte-specific member of the tumor necrosis factor or nerve growth factor receptor family and/or the cell adhesion protein CD62L.

Another aspect of the invention is a composition comprising, consisting essentially of, or consisting of the enriched and, optionally, expanded Tregs produced by the methods of the present invention.

In one embodiment, the composition may include a pharmaceutically acceptable carrier. In another aspect, the composition includes at least one therapeutic agent for treatment of inflammation or autoimmunity. In another aspect, the composition includes at least one corticosteroid. In another aspect, the composition includes rapamycin.rdt Yet another embodiment of the present invention is a method of preventing or treating an immune disorder in a patient by administering to the individual any of the Treg cells produced by the methods of the present invention. In one aspect, the immune disorder is an autoimmune disorder. In another aspect, the immune disorder is one of systemic lupus erythematosus (SLE), rheumatoid arthritis, type 1 diabetes, multiple sclerosis (MS), aplastic anemia, and idiopathic thrombocytopenic purpura.

One aspect of the disclosure provides a therapeutic for treating Type 1 diabetes, aplastic anemia, graft transplantation, and graft-versus host disease (GVHD), and other autoimmune diseases. The therapeutic contains isolated T lymphocyte regulatory cells that express Foxp3 protein and at least one of LAP, CD121a (IL-1 receptor type 1), and CD 121b (IL-1 Receptor Type 2) and LRRC32 (GARP). In some embodiments, the isolated T regulatory cells are human T regulatory cells isolated from the patient to be treated. In some embodiments, the isolated T regulatory cells are nonresponsive to TCR stimulation in vitro. In other embodiments, the cells produce a minimal level of IL-2, IL-17, IL-4, or interferon-gamma. In certain embodiments, the T lymphocyte regulatory cells suppress proliferative responses in CD4+ CD25− T cells. The therapeutic may be administered with other known immunosuppressive therapies.

Yet another embodiment of the invention is a method of treating or preventing a transplant rejection in an individual, by administrating to the individual any of the Treg cells produced by the methods of the present invention. In one aspect, the transplant rejection is graft-versus-host-disease (GVHD).

Another aspect of the disclosure provides a method of diminishing the symptoms of Type 1 diabetes, aplastic anemia, graft transplantation, and graft-versus host disease (GVHD), and other autoimmune diseases by administering lymphocytic cells that express Foxp3 protein and at least one of LAP, CD121a (IL-1 receptor type 1), and CD 121b (IL-1 Receptor Type 2) and LRRC32 (GARP). In some embodiments, the isolated T regulatory cells are human T regulatory cells isolated form the patient to be treated. In embodiments, the isolated T regulatory cells are nonresponsive to T cell receptor (TCR) stimulation in vitro. In other embodiments, the cells produce a minimal level of IL-2, IL-17, IL-4, or interferon-gamma. In certain embodiments, the T lymphocyte regulatory cells suppress proliferative responses in CD4+ CD25− T cells. The therapeutic may be administered with other known immunosuppressive therapies.

Another aspect of the invention is the use of any of the Treg cells produced by the methods of the present invention in the preparation of a medicament for the prevention or treatment of an immune disorder.

Another aspect of the invention is the use of any of the Treg cells produced by the methods of the present invention in the preparation of a medicament for the prevention or treatment of a transplant rejection.

BRIEF DESCRIPTION OF THE FIGURES OF THE INVENTION

FIG. 1 shows CD25 and CD127 allow for purification of FOXP3+ Tregs (JPG, 213 KB): (A) Flow cytometric correlation of the expression of different cell surface antigens with FOXP3 expression on freshly explanted CD4+ T cells from three healthy adult donors (D1, D2, D3); (B) Correlation of CD127$^{hi}$ and CD127$^{low}$ with expression of CD25 and FOXP3 (Data is from one representative donor of 6); (C and D) Post-sort analysis of the percentage of FOXP3+ T cells purified by FACS-sorting the top 2% CD25+ T cells, by bead-sorting through depletion of CD127+ cells and positive selection of CD25+ cells, and by bead-sorting through positive selection of CD25.

Figure 2:
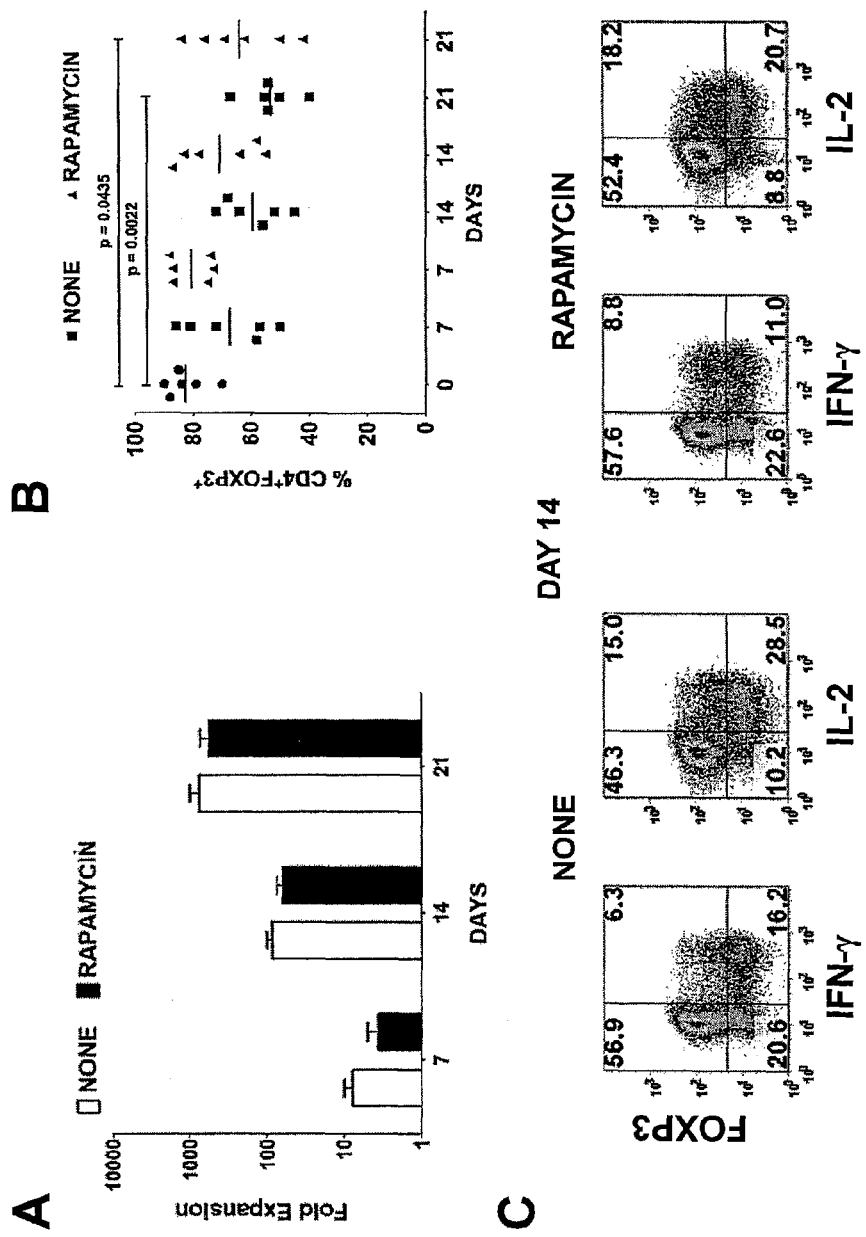

FIG. 2 shows Treg expansion cultures contain cytokine-producing FOXP3− and FOXP3+ non-Tregs: (A) Fold expansion of magnetic bead-purified CD4+CD127$^{low}$CD25+ T cells from 6 donors after stimulation with anti-CD3/CD28 and IL-2 in the absence or presence of rapamycin. Error bars represent SEM; (B) Percentage of CD4+FOXP3+ T cells in the starting population and after expansion of CD4+ CD127$^{low}$CD25+ T cells as described in panel A. Horizontal lines represent the mean of each group; (C) Day 14 expansion cultures generated in the absence or presence of rapamycin were restimulated for 5 hours with PMA/ionomycin. IFN-γ and IL-2 production was evaluated by intracellular staining Data are representative of 6 independent experiments. The number in each quadrant represents the percentage of total population.

Figure 3:
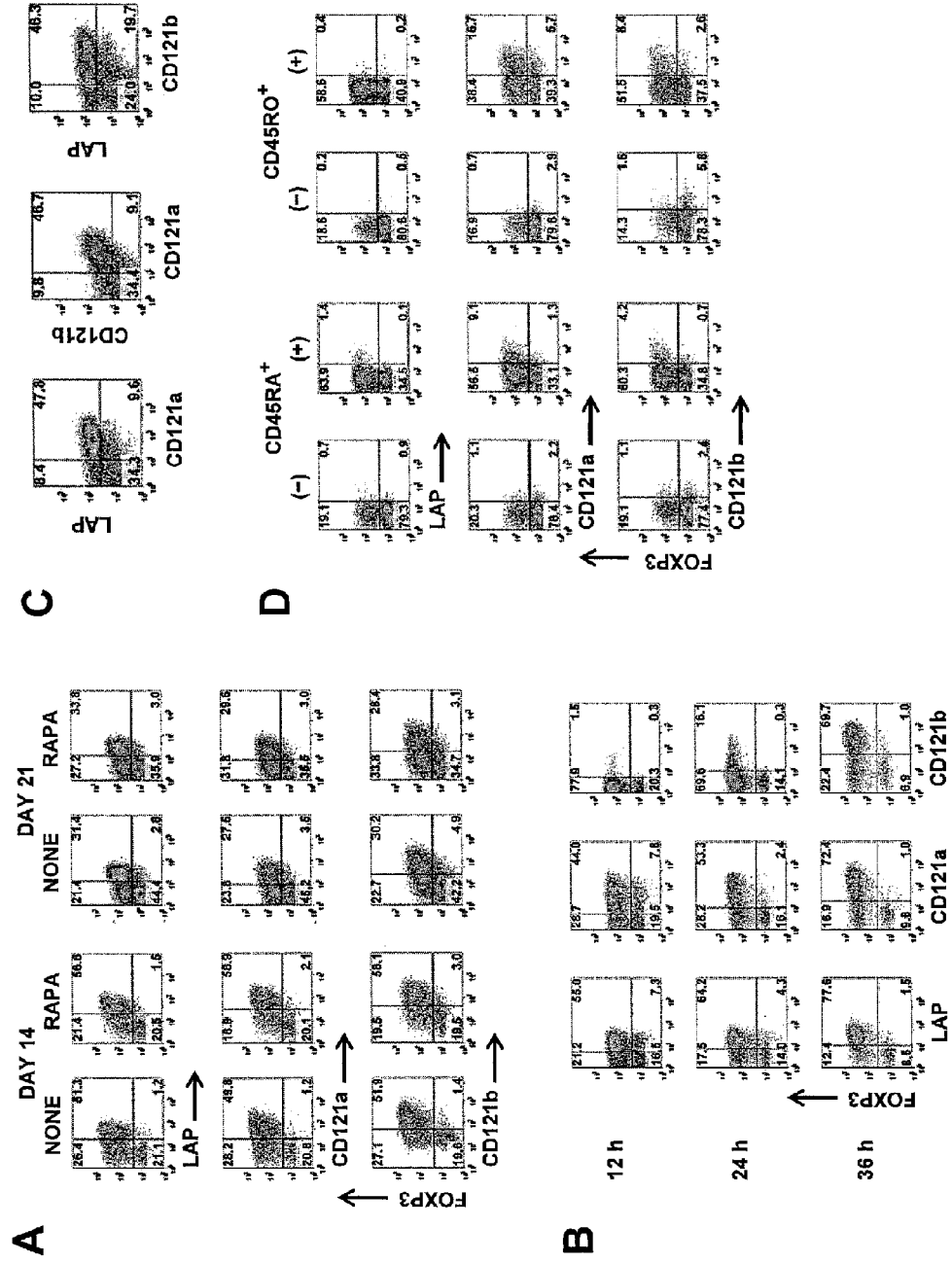

FIG. 3 shows the selective expression of LAP, CD121a, and CD121b on activated Tregs: (A) Flow cytometric analysis of surface LAP, CD121a, and CD121b and intracellular FOXP3 expression on day 14 and day 21. Treg expansion cultures after restimulation for 48 hours with anti-CD3/CD28 (data are from 1 representative donor of 6); (B) Kinetics of LAP, CD121a, and CD121b expression on fresh Tregs stimulated with anti-CD3/CD28 and 100 U/mL IL-2; (C) costaining of LAP, CD121a, and CD121b on 48-hour restimulated day 14 cultures (data are from 1 donor representative of 6); (D) Expression of LAP, CD121a, and CD121b on 48-hour restimulated day 14 CD4+CD25− CD127+CD45RA+ and CD45RO+ T cells previously stimulated on day 0 with anti-CD3/CD28 and IL-2 for 5 days in the absence (−) or presence (+) of TGFβ1 and rested in IL-2 until day 12. Data are representative of 3 independent experiments. Number in each quadrant represents the percentage of total population.

Figure 4:
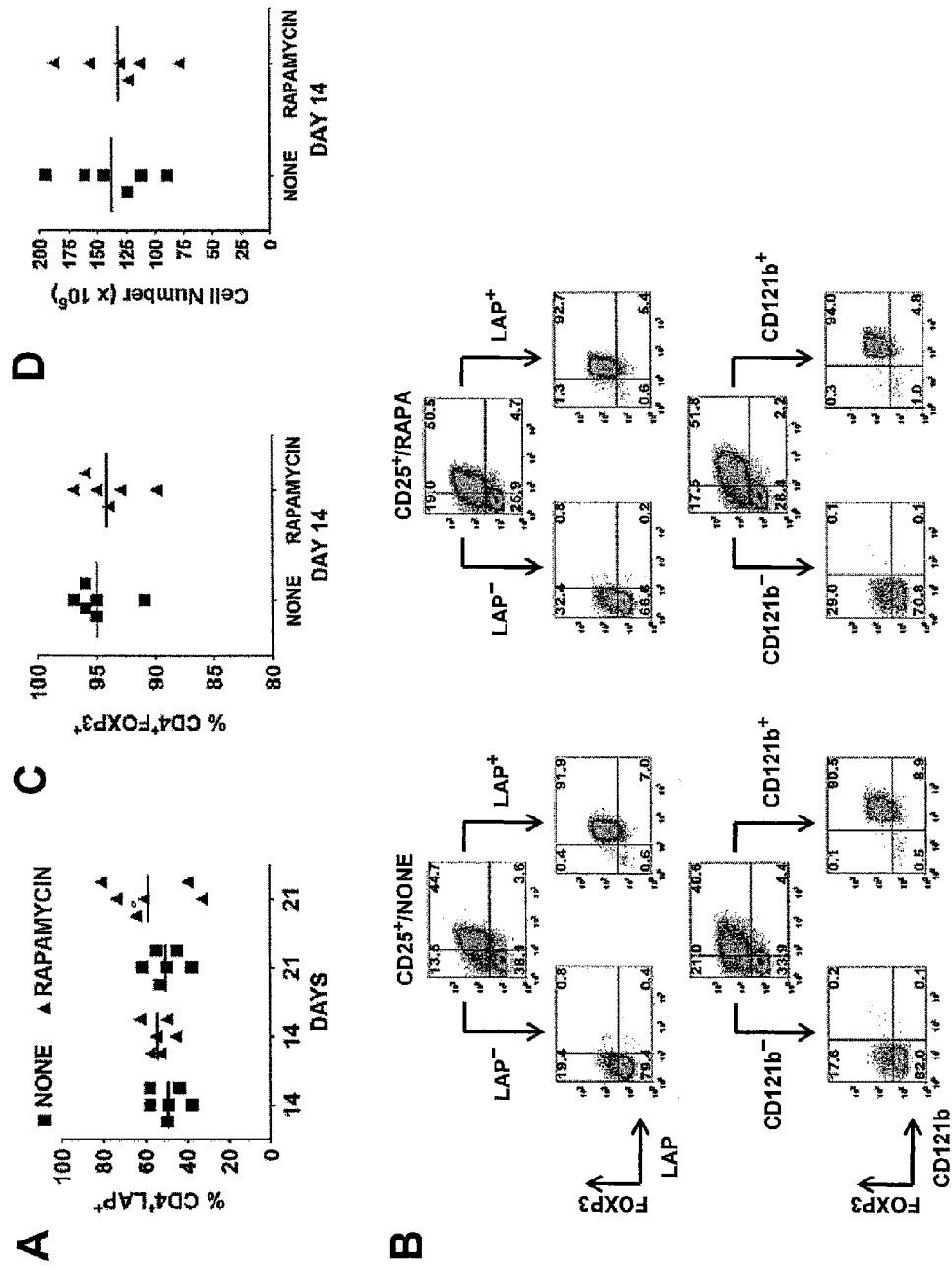

FIG. 4 shows the selective expression of LAP and CD121b allows for separation of Tregs from non-Tregs in ex vivo expansion cultures: (A) Percentage of CD4$^+$LAP$^+$ cells after 48 hours of restimulation of day 14 and 21 expansion cultures. (B) Day 14 expansion cultures generated in the absence (CD25$^+$/NONE) or presence (CD25$^+$/RAPA) of rapamycin were restimulated for 48 hours with anti-CD3/CD28. LAP$^+$/LAP$^-$ and CD121b$^+$/CD121b$^-$ fractions were then purified with magnetic beads and analyzed by flow cytometry for FOXP3 expression. Number in each quadrant represents the percentage of total population; (C) Percentage of CD4$^+$ FOXP3$^+$ and (D) cell yield after purification of LAP$^+$ cells from restimulated 14-day expansion cultures. Horizontal lines in panels A, C, and D represent the mean of each group.

Figure 5:
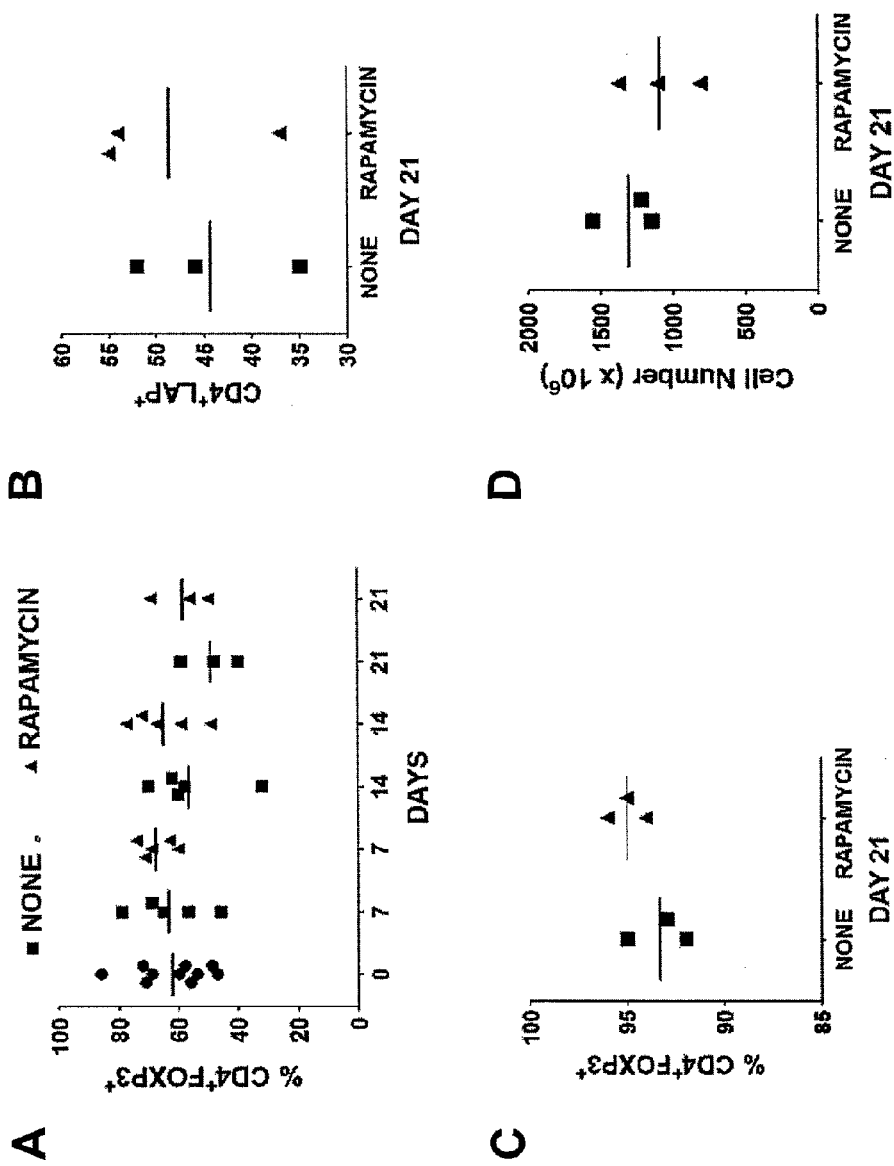

FIG. 5 shows the repurification of Tregs with anti-LAP in expansion culture using one-step CD25 selection method (JPG, 52.1 KB): (A) Percentage of CD4$^+$FOXP3$^+$ T cells in the starting population and following expansion of CD25$^+$ cells in the absence (NONE) or presence of rapamycin over a 21 d period; (B) Percentage of LAP$^+$ cells after 48 h restimulation of day 21 expansion cultures; (C) Percentage of CD4$^+$ FOXP3$^+$ and (D) cell yield following purification of LAP$^+$ cells.

Figure 6:
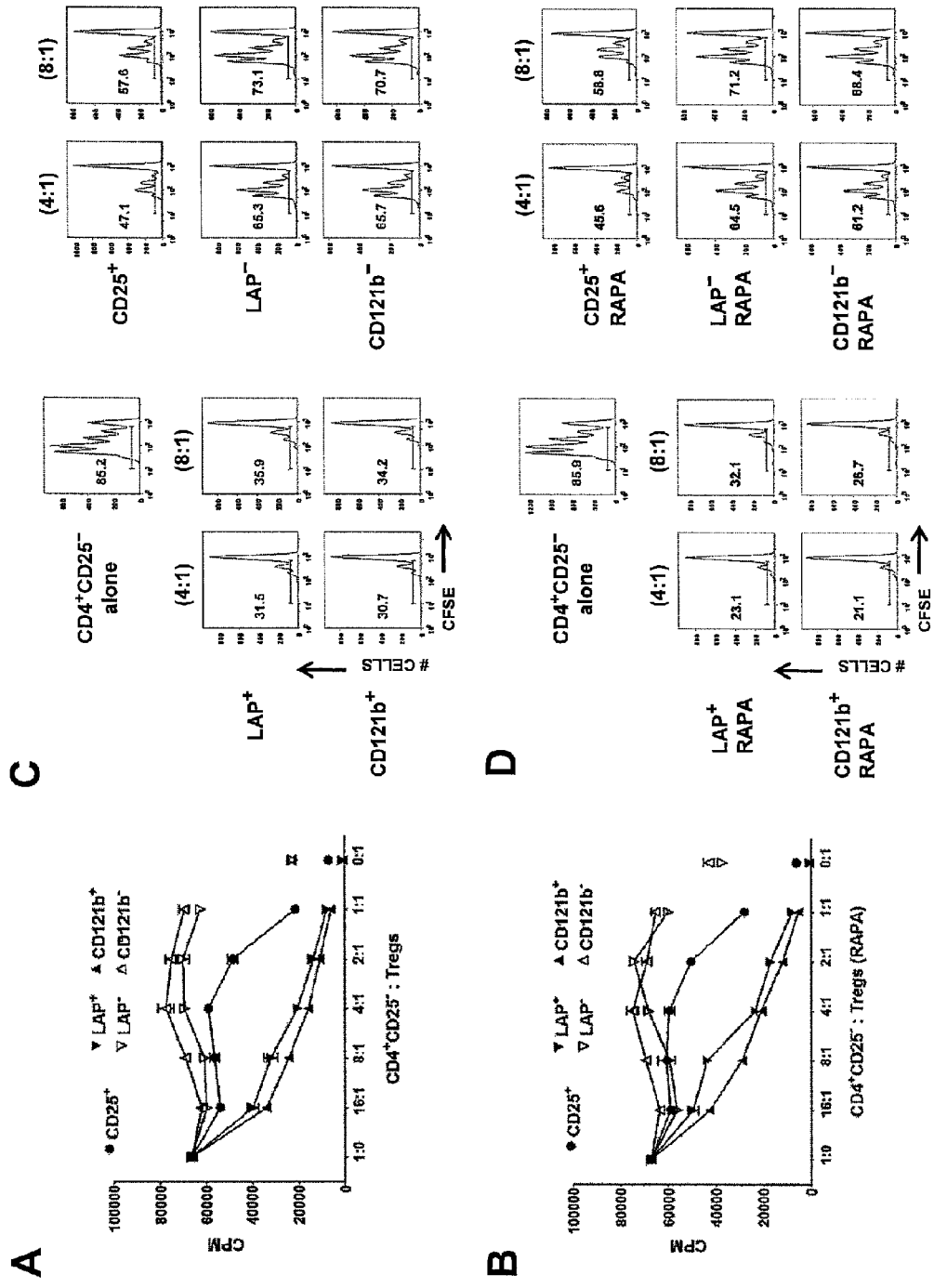

FIG. 6 shows that LAP$^+$ and CD121b$^+$ Tregs are anergic and manifest potent T-suppressor activity. CD4$^+$CD25$^-$ T cells were stimulated with anti-CD3 and APCs alone (■) or in the presence of various numbers of unseparated CD25$^+$ or purified LAP$^+$, LAP$^-$, CD121b$^+$, and CD121b$^-$ cells from 48 hours of restimulated day 14 cultures generated in the absence (A) or presence (B) of rapamycin. Error bars represent SEM. $^3$H-TdR incorporation was determined after 72 hours of stimulation. CFSE-labeled CD4$^+$CD25$^-$ T cells were stimulated with anti-CD3 and APCs alone or in the presence of unseparated CD25$^+$ or purified LAP$^+$, LAP$^-$, CD121b$^+$, and CD121b$^-$ cells from 48-hour restimulated day 14 cultures generated in the absence (C) or presence (D) of rapamycin. Cocultures were performed at responder to suppressor ratios of 4:1 and 8:1. CFSE dilution was measured by FACS analysis after 72 hours of culture. Number in each quadrant represents percentage of dividing cells from the total population. Data are from 1 donor representative of 6.

Figure 7:
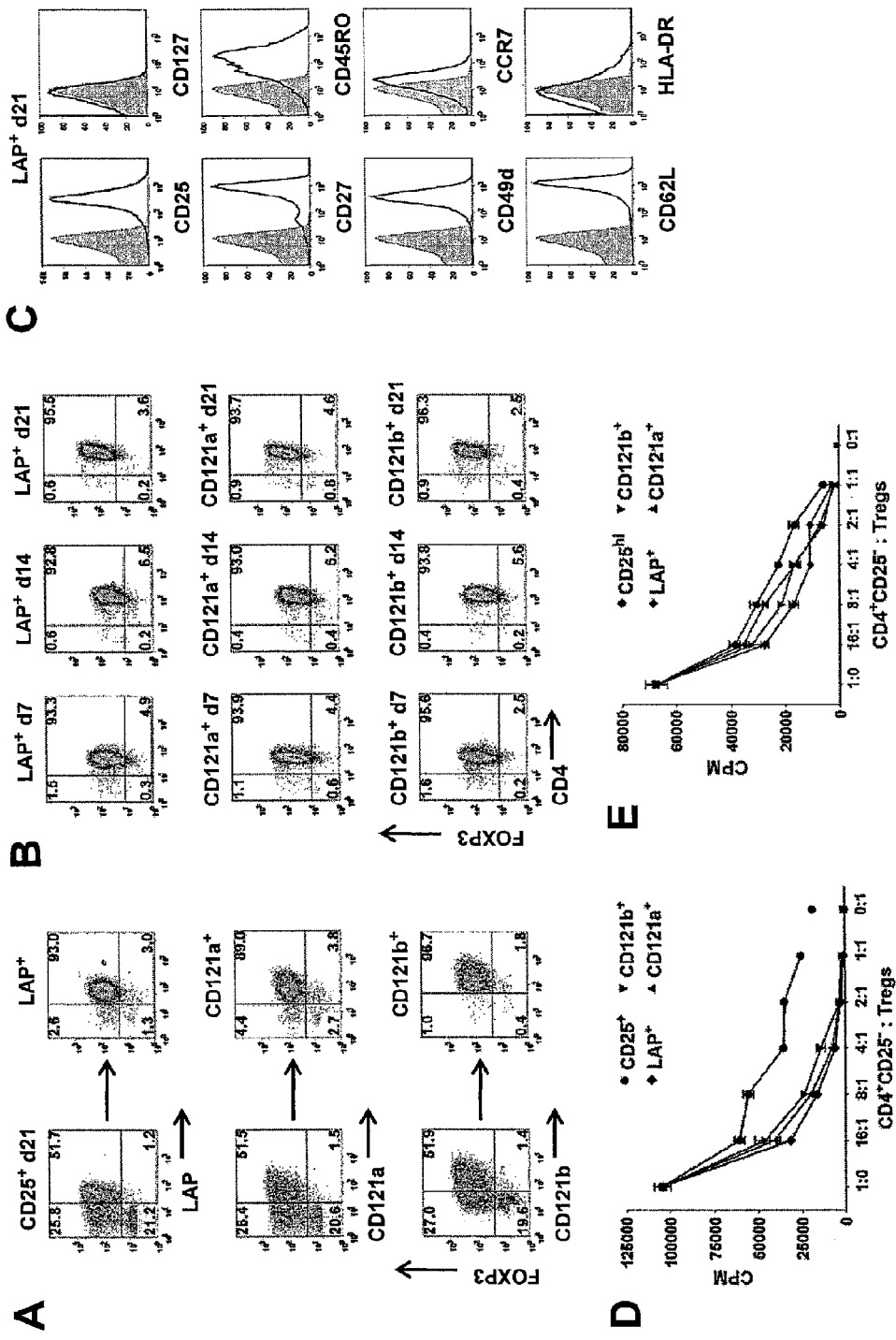

FIG. 7 shows that LAP$^+$, CD121a$^+$, and CD121b$^+$ Tregs maintain purity, suppressive function, and phenotype after expansion: (A) Expression and purification based on LAP, CD121a, and CD121b on 48-hour restimulated CD25+ cells initially obtained with one-step CD25 selection method and expanded for 21 days; (B) Analysis of FOXP3 during an additional 21 more days of expansion for LAP$^+$, CD121a$^+$, and CD121b$^+$ Tregs with anti-CD3/CD28 Dynabeads and IL-2 and, (C) their typical Treg surface markers at the end of the 21-day expansion (42 total days in culture). Data are representative of CD121a$^+$ and CD121b$^+$ Tregs as well. Numbers in quadrants in panels A and B represent percentage of total population; (D) In vitro suppression assay of day 21 unseparated CD25$^+$ cells (CD25+) and postpurified LAP$^+$, CD121a$^+$, and CD121b$^+$ Tregs from panel A. Error bars represent SEM; (E) In vitro suppression assay of fresh Tregs (CD25$^{hi}$) and 21-day expanded LAP$^+$, CD121a$^+$, and CD121b$^+$ Tregs from panel B. Error bars represent SEM.

Figure 8:
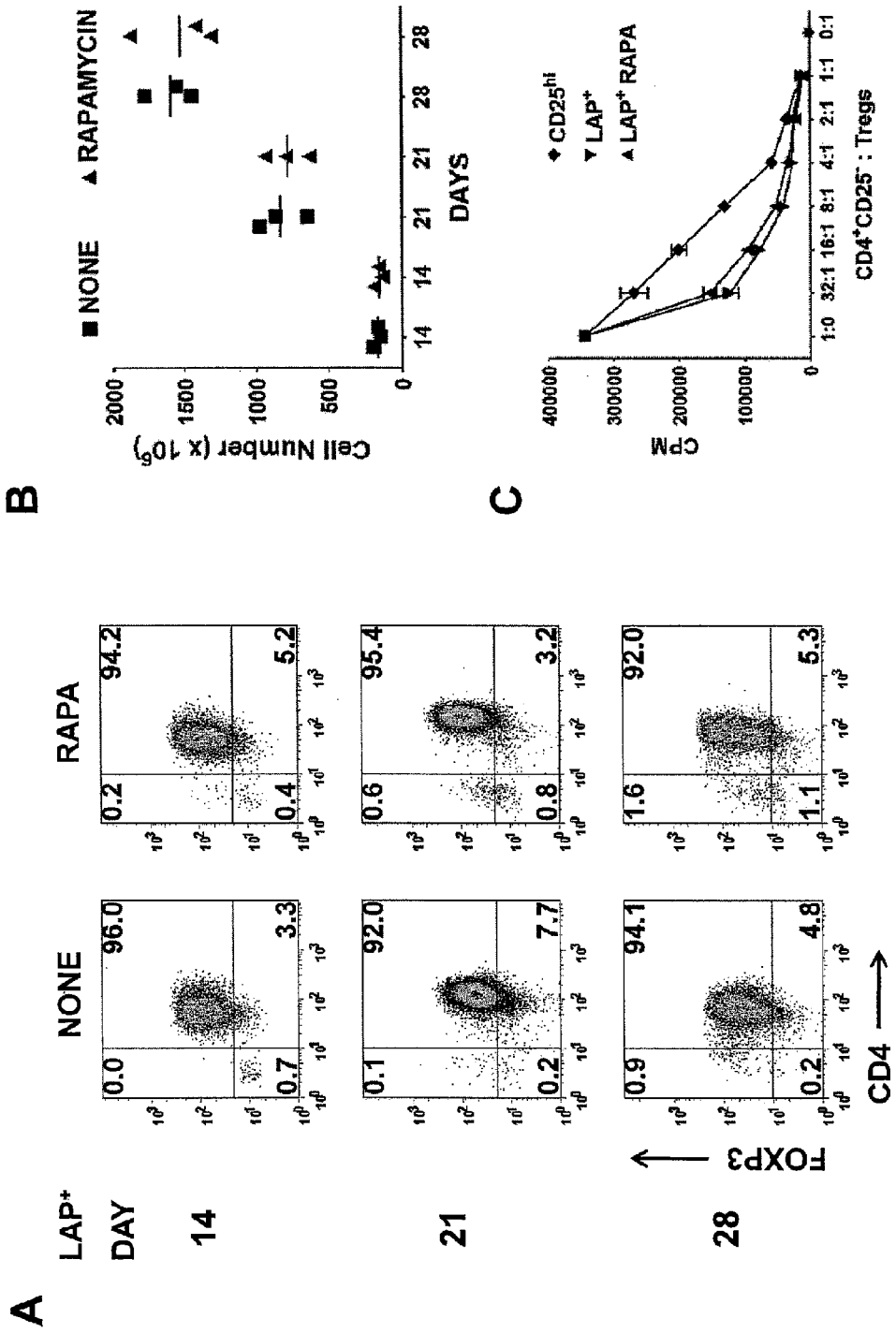

FIG. 8 shows purified LAP$^+$ Tregs can be further expanded to obtain a greater cell yield while maintaining FOXP3 purity (JPG, 73.3 KB): (A) FOXP3 purity and (B) cell yield of post-sort bead purified LAP$^+$ Tregs on day 14 and on day 21 and 28 with continued expansion using anti-CD3/CD28 Dynabeads and IL-2; (C) In vitro suppression assay of fresh Tregs (CD25$^{hi}$) and day 28 expanded LAP$^+$ Tregs.

Figure 9:
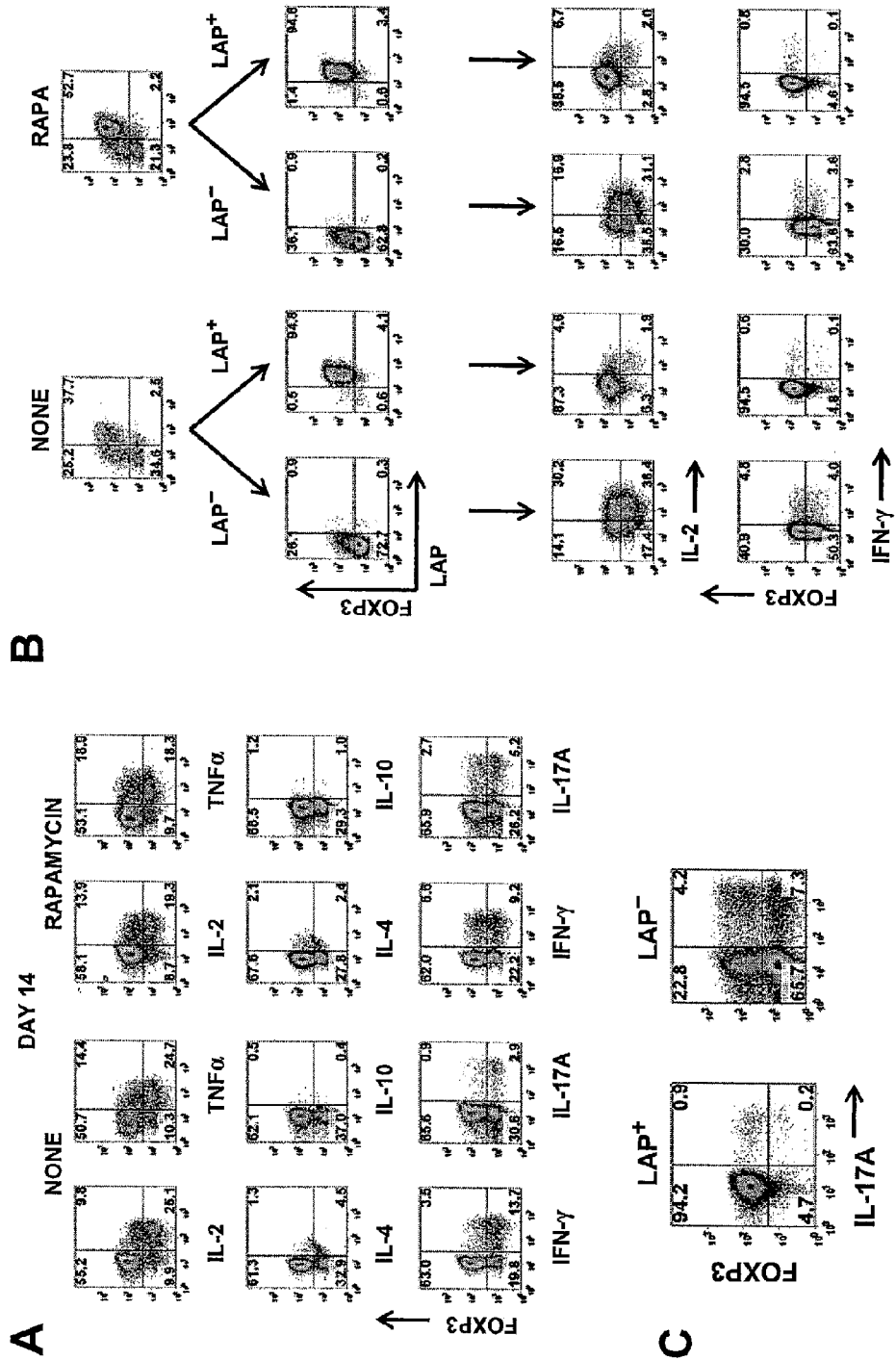

FIG. 9 shows the majority of cytokine producing effector T cells are found in the FOXP3$^-$ and FOXP3$^+$ non-Tregs (JPG, 196 KB): (A) Day 14 expansion cultures in the absence (NONE) or presence of rapamycin were restimulated for 5 h with PMA/ionomycin and analyzed by intracellular staining for cytokine production and FOXP3; (B) LAP$^+$ and LAP$^-$ cells were purified 48 h after restimulation of day 14 expansion cultures generated in the absence (NONE) or presence (RAPA) of rapamycin. The purified cell populations were then restimulated for 5 h with PMA/ionomycin and production of IL-2 and IFN-γ measured by intracellular staining; (C) LAP$^+$ and LAP$^-$ cells were purified 48 h after restimulation of day 14 expansion cultures and analyzed for IL-17 production. Data are representative of 3 independent experiments.

Figure 10:
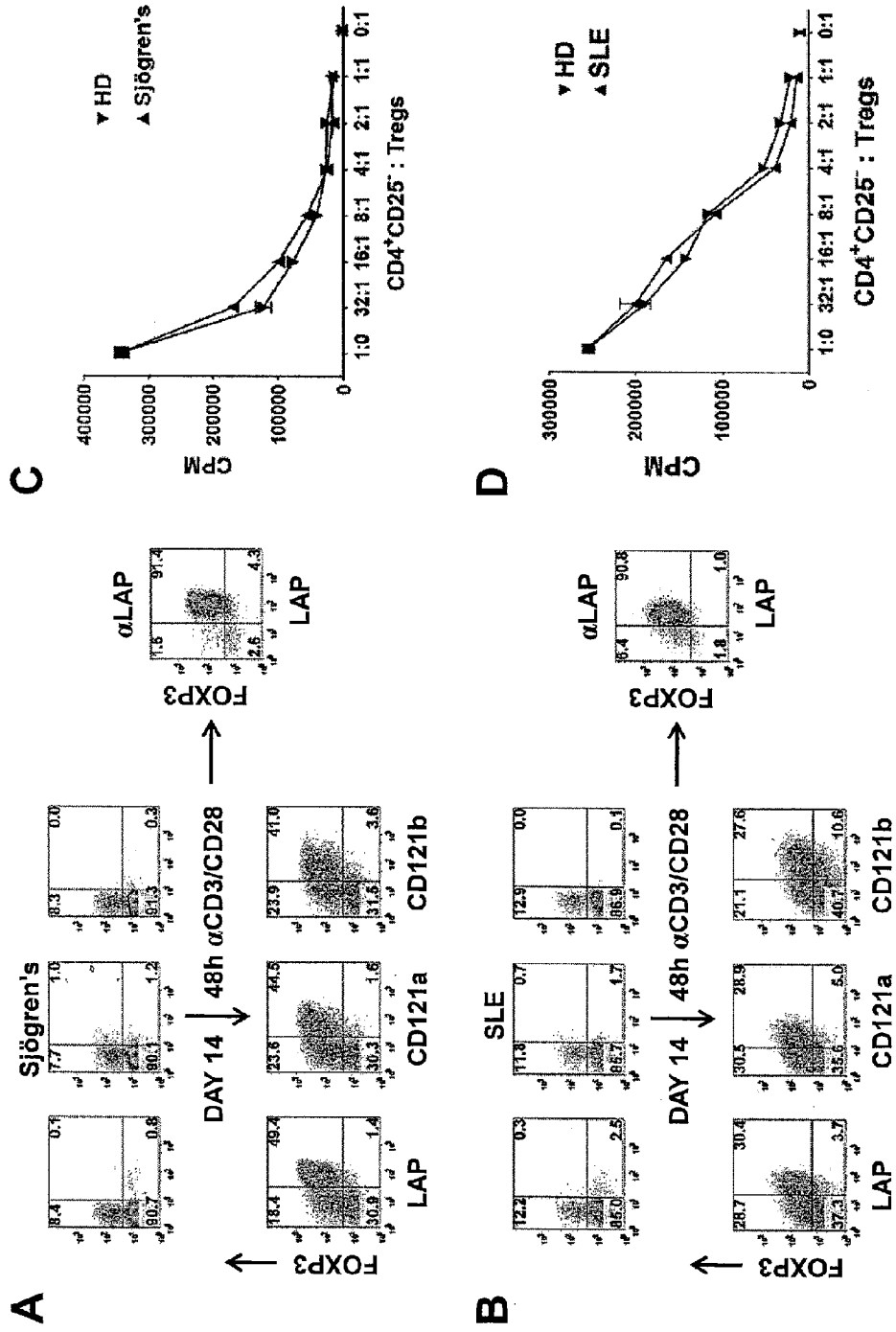

FIG. 10 shows the expansion and purification of Tregs from patients with Sjögren syndrome and SLE with 5 to 10 mL peripheral blood. Expression of LAP, CD121a, CD121b, and FOXP3 on CD4$^+$ T cells from a patient with (A) Sjögren syndrome or (B) SLE (top). Correlation of LAP, CD121a, and CD121b with FOXP3 on 48-hour restimulated CD25$^+$ cells from one-step CD25$^+$ selection method expanded for 14 days (bottom). Numbers in each quadrant represent percentage of total population. Right panel represents the FOXP3 purity after reisolation with anti-LAP from day 14—expanded CD25$^+$ cells of patients with Sjögren syndrome and SLE. In vitro suppression assay of LAP$^+$ Tregs from patient with (C) Sjögren syndrome or (D) SLE, comparing with LAP$^+$ Tregs from healthy control donors (HD). Data represent 1 of 3 patients with Sjögren syndrome and SLE. Error bars represent SEM.

Figure 11:
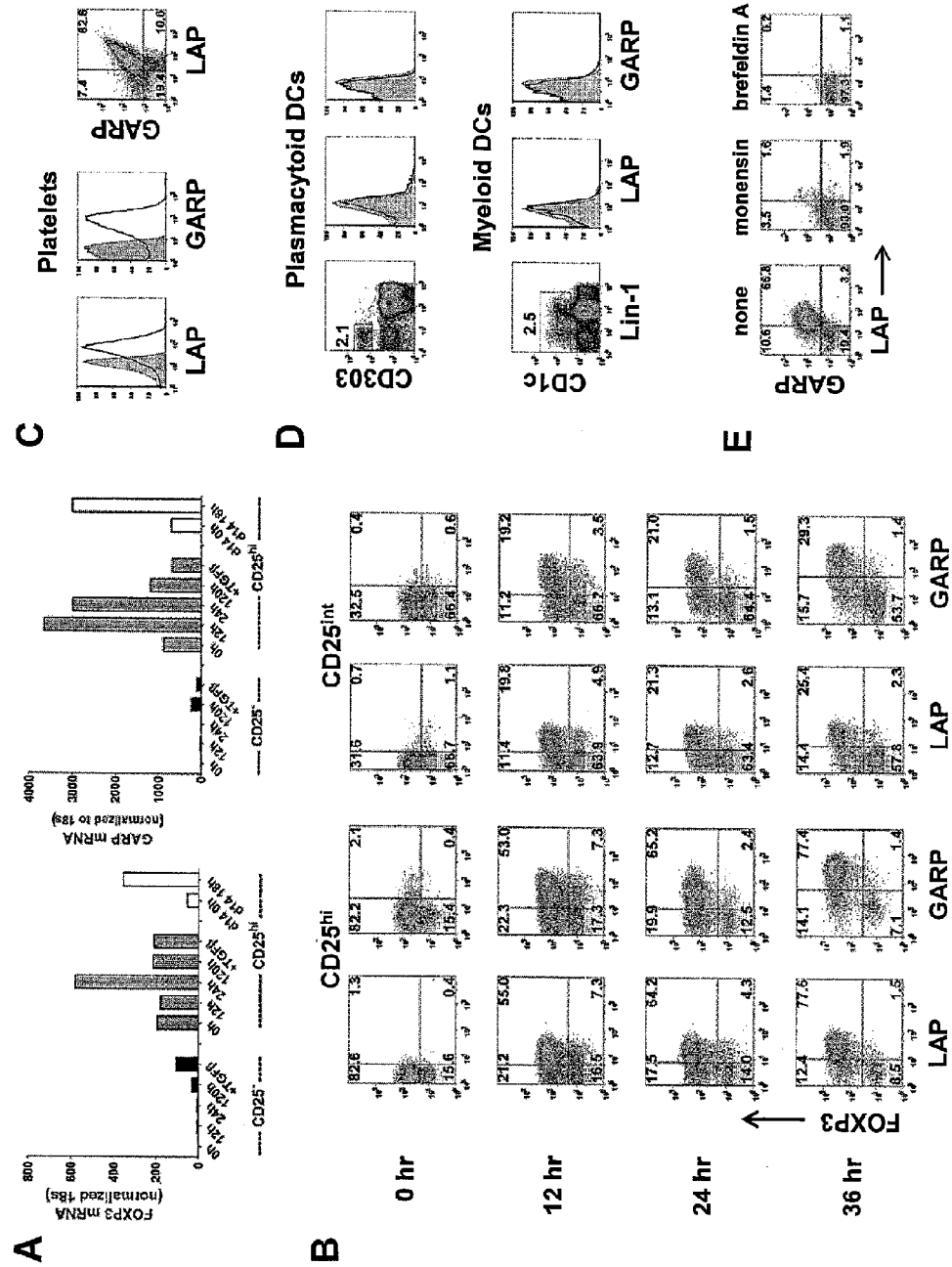

FIG. 11 shows that GARP and LAP are selectively expressed on activated FOXP3$^+$ Tregs and platelets: (A) Level of FOXP3 and GARP mRNA on fresh (0 h) and activated CD4$^+$CD25$^-$ T cells and Tregs (CD25$^{hi}$) at 12, 24, 120 h, or 120 h with TGF-β1. Tregs were rested until day 14 (0 h) and restimulated for 18 h; (B) Flow cytometric analysis of surface LAP, GARP and intracellular FOXP3 on fresh (0 h) and activated Tregs (CD25$^{hi}$) and CD4$^+$CD25$^{int}$ T cells; (C) Surface staining of LAP and GARP on platelets based on FSC/SSC and CD61 expression; (D) LAP and GARP surface staining of plasmacytoid and myeloid DCs from PBMCs by gating on CD303$^+$Lin-1$^-$ and CD1c$^+$, respectively; (E) Surface LAP and GARP expression on Tregs after 12 h activation in the absence (none) or presence of monensin or brefeldin A for the last 8 h; Data are representative of 3 independent experiments. Numbers indicate percentage in each quadrant for B-E.

Figure 12:
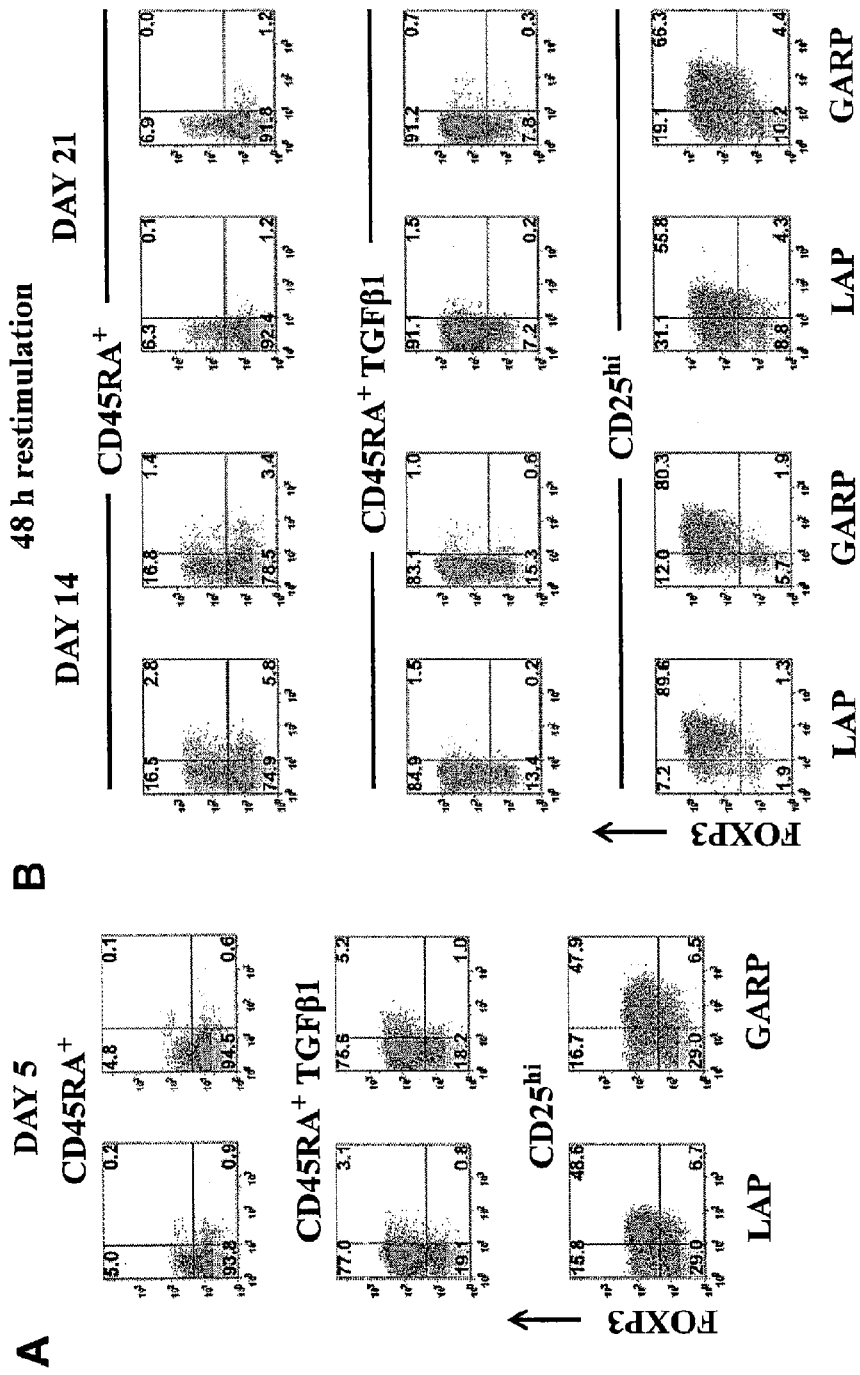

FIG. 12 shows that surface GARP and LAP are selectively expressed on activated Tregs (CD25$^{hi}$) and not on FOXP3$^-$ or TGFβ-induced FOXP3$^+$ T cells: (A) Naïve T cells (CD45RA$^+$) were stimulated in the absence or presence of TGFβ-1 and Tregs in the absence of TGF-β1 for 5 days and evaluated for the expression of FOXP3 and surface GARP and LAP; (B) The cells were then removed from stimulation and rested in IL-2 medium. On day 12, the cells were restimulated for 48 h in the absence of TGF-β1 and then rested again in IL-2 medium until day 19 for another round of restimulation. Intracellular FOXP3 and surface GARP and LAP were evaluated after 48 h restimulation during each cycle. Data are representative of 3 independent experiments. Numbers indicate percentage in each quadrant.

DETAILED DESCRIPTION OF THE INVENTION

The present invention relates to methods of obtaining and using immunomodulating pharmacotherapies for use in adoptive immunotherapy to prevent or treat autoimmune encephalomyelitis, type 1 diabetes, SLE, autoimmune gastritis, inflammatory bowel disease, aplastic anemia, graft rejection, and GVHD. Methods are provided for the detection, identification and isolation of activated FOXP3+ Tregs. It is shown in this disclosure that FOXP3+ regulatory T cells (Tregs) selectively express cell surface proteins latency-associated peptide (LAP), IL-1 receptor type I (CD121a), IL-1 receptor type II (CD121b) and GARP (LRRC32).

TGF-β family members are highly pleiotropic cytokines normally found in the latent form associated with latency-associated peptide (LAP). This latent complex can associate with latent TGF-β-binding protein (LTBP) to produce a large latent form. Latent TGF-β is also found on the surface of activated FOXP3$^+$ regulatory T cells (Tregs), but it is has remained unclear how it is anchored to the cell membrane. In addition, latent TGF-β can be expressed on the membrane of many cell types, including megakaryocytes, platelets, immature dendritic cells (DCs), and activated FOXP3$^+$ regulatory T cells (Tregs), and has important functions in tissue healing and immune regulation.

The GARP (or LRRC32) gene consists of 662 aa and encodes an 80-kDa transmembrane protein with an extracellular region composed primarily of 20 leucine-rich repeats. This disclosure shows that GARP is critical for the surface expression of latent TGF-β by binding to the complex and functioning as its cell surface receptor. GARP functions as a carrier and cell surface receptor for latent TGF-β1, and activated Tregs co-express latent TGF-β and GARP on their membranes, making GARP another cell surface protein that is selectively expressed on the surface of FOXP3+ regulatory T cells, similar to latency-associated peptide (LAP), IL-1 receptor type I (CD121a), IL-1 receptor type II (CD121b).

CD4$^+$FOXP3$^+$ regulatory T cells represent a mixture of both thymic-derived and FOXP3$^+$ Tregs that are generated at peripheral sites. In humans only those CD4$^+$T$^{hi}$ cells expressing high levels of CD25 are uniformly FOXP3$^+$. Human Tregs can be expanded ex vivo, and their use for the cell-based tolerogenic therapy of autoimmune diseases, graft rejection, or GVHD has been advocated. A major obstacle for the use of human Tregs in cell-based therapy to date has been the difficulty of obtaining a highly pure population after ex vivo expansion. A CD4$^+$FOXP3$^+$ population of greater than 90% purity can be isolated by fluorescence-activated cell sorting (FACS) of the top 2% to 4% of CD4$^+$ T cells with high CD25 expression (CD25$^{hi}$) from peripheral blood, but frequently the percentage of FOXP3$^+$ T cells decreases to 75% after 1 week and to 50% after 2 weeks of expansion by stimulation with anti-CD3/CD28 and IL-2.

The expression of FOXP3 can be induced by T-cell receptor (TCR) stimulation of human CD4$^+$CD25$^-$FOXP3$^-$ T cells in the presence of TGFβ, but the induced cells lack all the functional properties of Tregs. Because TGFβ is present in the serum used for cultures, a similar induction of FOXP3 expression in contaminating FOXP3$^-$T cells may occur during expansion cultures of partially purified Tregs. Although the expanded population might appear to be highly enriched in FOXP3$^+$ cells, many of these cells may be induced FOXP3$^+$ cells that lack Treg functions.

One aspect of the present invention is a method of using unique cell-surface markers to purify FOXP3$^+$ Tregs from ex vivo expansion cultures. In one embodiment, the purification method starts with leukapheresis preparations and uses only magnetic bead targeting reagents to isolate FOXP3$^+$ Tregs from an ex vivo expansion culture. In one embodiment, the cell-surface marker is any one of latency-associated peptide (LAP), IL-1 receptor type I (CD121a), IL-1 receptor type II (CD121b) and GARP (LRRC32) which are selectively expressed on activated Tregs, but not on activated CD4+FOXP3$^-$ or induced FOXP3$^+$ non-regulatory T cells. The Treg cell population isolated using this method is composed of greater than 70% FOXP3$^+$ cells, and preferably greater than 80% FOXP3$^+$ cells, and preferably greater than 90% FOXP3$^+$ cells, and preferably greater than 95% FOXP3$^+$ cells, that are highly anergic and suppressive in vitro. This method provides an important advance for the preparation of Tregs for cell-based immunotherapy to treat or prevent autoimmunity and transplantation-related complications. In one embodiment, this methodology may be used to expand and purify Tregs from about 1 mL to about 20 mL of blood, and preferably from about 5 mL to about 10 mL of blood to achieve high numbers and purity. This ability to isolate a highly anergic population of primarily FOXP3$^+$ cells from low volumes of blood is particularly advantageous given the limitation of human blood samples, particularly in the pediatric population, and the importance of obtaining a highly purified Treg population for functional and genomic analyses.

In one aspect, the invention provides methods of making an isolated population of FOXP3+ T-cells. In one embodiment, the population is isolated by obtaining a biological sample containing T-cells and isolating the FOXP3+ T-cells from other cells in the biological sample, including, but not limited to, activated CD4+FOXP3$^-$ or induced FOXP3+ non-regulatory cells.

In another aspect, the invention provides kits containing materials specifically useful in performing the methods of isolating populations of FOXP3+ T-cells of the present invention. A kit for identifying or isolating a FOXP3+ T-cells, for example, may include an antibody that binds any one of latency-associated peptide (LAP), IL-1 receptor type I (CD121a), IL-1 receptor type II (CD121b) and GARP (LRRC32). The label is preferably labeled (e.g., a fluorescent, magnetic or isotopically label). In addition, the kit may further provide instructions or reagents for formulating the T-cell population in a suitable media or for expanding the T-cell population ex vivo or for contacting with cells in vivo or in vitro.

In another aspect, the invention provides methods of isolating FOXP3$^+$ T-cells by means of immunologic selection, and using these isolated regulatory T cells as a means of adoptive immunotherapy, such as in the treatment or study of autoimmunity, GVHD or transplant organ preparation or rejection.

In another aspect, the invention provides methods of utilizing FOXP3$^+$ T-cells isolated by immunologic selection, to prepare compositions such as pharmaceutical compositions or medicaments for use in the treatment of autoimmunity, GVHD or transplant organ preparation or rejection.

Unless otherwise stated, the following terms used in the specification and claims have the meanings given below.

It is noted here that as used in this specification and the appended claims, the singular forms "a," "an," and "the" include plural reference unless the context clearly dictates otherwise.

By a "population of cells" is meant a plurality of cells, preferably at least $10^3$, $10^4$, $10^5$, $10^6$, $10^7$, $10^8$, $10^9$, $10^{10}$, or $10^{11}$ cells. The population in some embodiments has from $10^5$ to $10^7$ cells, $10^6$ to $10^8$ cells, or from $10^8$ to $10^{11}$ cells, or $10^{10}$ to $10^{12}$ cells.

As used herein, the term "sample" or "biological sample" refers to tissues or body fluids removed from a mammal, preferably a human, and which contain T cells, including, but not limited to, FOXP3+ T-cells from other cells in the biological sample, including, but not limited to, activated CD4+

FOXP3⁻ or induced FOXP3+ cells. Samples preferably are blood and blood fractions, including peripheral blood. The biological sample is drawn from the body of a mammal, such as a human, and may be blood, cord blood, or similar tissues or cells. Methods for obtaining such samples are well known to workers in the fields of cellular immunology and surgery. They include sampling blood in well known ways, or obtaining biopsies from the thymus or other tissue or organ.

The term "isolated" with regard to a population of cells as used herein refers to a cell population which either has no naturally-occurring counterpart or has been separated or purified from other components, including other cell types, which naturally accompany it, e.g., in normal or diseased tissues such as lung, kidney, or placenta, tumor tissue such as colon cancer tissue, or body fluids such as blood, serum, or urine. Typically, an isolated cell population is at least two-fold, four-fold, or eight-fold enriched for a specified cell type when compared to the natural source from which the population was obtained.

A population or subpopulation of cells which is "substantially" of a specified cell type is one which has a count of the specified cell type which is at least 50%, 75%, 80%, 90%, 95% or, most preferably, 98% or 99% of the total cell count of the population or subpopulation or one which is at least two-fold, four-fold, eight-fold, ten-fold or 20-fold enriched for a specified cell type as compared to a source population of the specified cell type. A substantially pure population may be at least about 50% FOXP3$^+$ T-cells in the population, at least about 75% FOXP3$^+$ T-cells in the population, at least about 80% FOXP3$^+$ T-cells in the population, at least about 90% FOXP3$^+$ T-cells in the population, or more.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Specific binding to an antibody under such conditions requires an antibody that is selected for its specificity for a particular protein. For example, polyclonal antibodies can be selected to obtain only those polyclonal antibodies that are specifically immunoreactive with the selected antigen and not with other proteins. This selection may be achieved by subtracting out antibodies that cross-react with other molecules.

A "label" or a "detectable moiety" is covalently or noncovalently attached to the antibody. A label may be detectable by spectroscopic, photochemical, biochemical, immunochemical, chemical, or other physical means. Particularly useful labels are fluorescent dyes. Methods of attaching labels to antibodies are well known to those of ordinary skill in the art. Particularly preferred labels are those which are attached to the antibody by a linker which can be readily cleaved or separated or subject to hydrolysis by contact with a predetermined enzyme under physiological conditions. The antibody may also be conjugated with a magnetic particle, such as a paramagnetic microbead (Miltenyi Biotec, Germany). An activated T cell bound by a magnetically labeled antibody may be isolated using techniques including, but not limited to, magnetic cell sorting. Suitably labeled antibodies to any one of latency-associated peptide (LAP), IL-1 receptor type I (CD121a), IL-1 receptor type II (CD121b) and GARP (LRRC32) as well as many other cell surface proteins may be produced by methods well known in the art and in some instances are commercially available. The antibody may be labeled before or after contact with the sample or before or after contact with the biological marker protein. The antibody that binds the biological marker protein may be labeled by contact with a labeled antibody which binds to the antibody that binds to the biological marker protein.

As used herein the term "immunologic selection" refers to selecting, and optionally, to quantitating the number of, cells displaying specific cell surface proteins or biomarkers or combinations of specific cell surface biomarkers from a sample, or of cells comprising a cell surface protein of interest in a sample, by specific binding of the protein to an antibody or fragment thereof. Methods of immunologic selection are known in the art. Preferred immunologic selection methods useful in the methods of the present invention include cell staining, flow cytometry, fluorescence-activated cell sorting (FACS), magnetic bead purification, and the like.

According to one aspect, the present invention provides a method for generating a population of FOXP3$^+$ Tregs by obtaining a biological sample containing T cells from a mammal and isolating a population of FOXP3$^+$ Tregs from the sample. Preferably the mammal is a human. The biological sample may contain T cells, including activated CD4+ FOXP3⁻ or induced FOXP3$^+$ cells. Samples preferably are blood and blood fractions, including peripheral blood. The biological sample is obtained from the body of a mammal, such as a human, and may be blood, cord blood, or similar tissues or cells.

In one embodiment, the biological sample or a fraction thereof maybe cultured in the presence of a chemical or cell that induces the expansion, proliferation, activation, or growth of T cells or specific populations of T cells. The cells may be expanded by use of growth factors and/or stromal cells associated with progenitor cell proliferation and differentiation. Such chemicals may include IFN-γ or rapamycin. Such cells may include donor-specific antigen presenting cells, or antigen presenting cells from a source separate from the donor.

In one embodiment, the isolation of the population of FoxP3$^+$ Tregs is a selection technique wherein the FoxP3$^+$ Tregs are separated from other cells in the biological sample. In a preferred embodiment, the selection is an immunological selection in which the FoxP3$^+$ Tregs in the biological sample are identified and separated from the sample by a labeled antibody or antibody fragment that specifically recognizes the FoxP3$^+$ Tregs or a specific component of the FoxP3$^+$ Tregs. The antibody label may be detectable by spectroscopic, photochemical, biochemical, immunochemical, chemical, or other physical means. Particularly useful labels are fluorescent dyes. Methods of attaching labels to antibodies are well known to those of ordinary skill in the art. Particularly preferred labels are those which are attached to the antibody by a linker which can be readily cleaved or separated or subject to hydrolysis by contact with a predetermined enzyme under physiological conditions.

In a preferred embodiment, the specific component recognized by the antibody or antibody fragment is at least one of latency-associated peptide (LAP), IL-1 receptor type I (CD121a), IL-1 receptor type II (CD121b) and GARP (LRRC32). In one embodiment, the immunological selection is a flow cytometry, fluorescence-activated cell sorting (FACS), or magnetic bead based isolation technique. In a preferred embodiment, the magnetic selection is conducted using an antibody or antibody fragment conjugated to a magnetic particle, such as a paramagnetic microbead (Miltenyi Biotec, Germany).

Detection or separation of the FoxP3+ Treg cell population typically relies on using immunologic specificity. Techniques providing accurate separation following immunological separation include fluorescence activated cell sorters, which can have varying degrees of sophistication, such as multiple color channels, low angle and obtuse light scattering detecting channels, impedance channels, etc. Any technique may be employed which is not unduly detrimental to the viability of the selected cells. Techniques for affinity separation may include magnetic separation, using antibody-coated magnetic beads, affinity chromatography, cytotoxic agents joined to a monoclonal antibody or used in conjunction with a monoclonal antibody, e.g. complement and cytotoxins, and "panning" with antibody attached to a solid matrix, e.g. plate, or other convenient technique.

The antibodies used as affinity reagents may be monoclonal or polyclonal, and may be produced by transgenic animals, immunized animals, immortalized human or animal B-cells, cells transfected with DNA vectors encoding the antibody or T cell receptor, etc. The antibodies may be conjugated with a label for use in detection or separation. Labels include magnetic beads, which allow for direct separation, biotin, which can be removed with avidin or streptavidin bound to a support, fluorochromes, which can be used with a fluorescence activated cell sorter, or the like, to allow for ease of separation of the particular cell type. Fluorochromes that find use include phycobiliproteins, e.g. phycoerythrin and allophycocyanins, fluorescein and Texas red. Frequently each antibody is labeled with a different fluorochrome, to permit independent sorting for each marker.

The antibodies are added to a suspension of cells, and incubated for a period of time sufficient to bind the available cell surface antigens. The incubation will usually be at least about 5 minutes and usually less than about 30 minutes. It is desirable to have a sufficient concentration of antibodies in the reaction mixture, such that the efficiency of the separation is not limited by lack of antibody. The appropriate concentration is determined by titration. The medium in which the cells are separated will be any medium which maintains the viability of the cells. A preferred medium is phosphate buffered saline containing from 0.1 to 0.5% BSA. Various media are commercially available and may be used according to the nature of the biological sample obtained, including Dulbecco's Modified Eagle Medium (DMEM), Hank's Basic Salt Solution (HBSS), Dulbecco's phosphate buffered saline (DPBS), RPMI, Iscove's medium, PBS with 5 mM EDTA, etc., frequently supplemented with fetal calf serum, BSA, HSA, etc.

Methods of sorting cells are well known to persons of ordinary skill in the art. Cell sorters generally are capable of separating a complex mixture of cells into fractions of a single cell type. Typically, the cells to be sorted are introduced as a thin stream of carrier liquid through the waist of one or more tightly focused laser beams. The scattered and fluorescence light from these interactions can be collected and analyzed to determine if there are events (e.g., the presence of a fluorescence signal indicating that a fluorophore-labeled monoclonal antibody is bound to the surface of a cell) that prompt the sorting of the cell by various means. More than one label can be monitored at a time. FACS (fluorescence activated cell sorters) can easily analyze cells at speeds greater than 200,000 events per second. Generally, the physics of the carrier fluid, however, and the statistics of distributing the cells among the droplets limits sort rates to about 50,000 cells per second. This combination of speed and reliable separation allows individual cells to be isolated for other uses.

Magnetic cell sorting may be performed using paramagnetic microbeads composed of iron oxide and a polysaccharide coat. The microbeads are preferably small enough to remain in colloidal suspension, which permits rapid, efficient binding to cell surface antigens. The microbeads preferably do not interfere with flow cytometry, are biodegradable, and have negligible effects on cellular functions. The antibody coupling to the microbeads may be direct or indirect, via a second antibody to a ligand such as fluorescein.

The labeled cells are then separated as to the expression of cell surface markers such as latency-associated peptide (LAP), IL-1 receptor type I (CD121a), IL-1 receptor type II (CD121b) and GARP (LRRC32). Optionally, the cell population is then further divided or purified into subsets based on the expression of these or other cell surface markers.

The separated cells may be collected in any appropriate medium that maintains the viability of the cells, usually having a cushion of serum at the bottom of the collection tube. Various media are commercially available and may be used according to the nature of the cells, including DMEM, HBSS, DPBS, RPMI, Iscove's medium, etc., frequently supplemented with fetal calf serum or human serum.

The invention also provides compositions comprising a population of cells wherein at least 50% of the cells of the composition are FoxP3$^+$ T cells. The percentage of FoxP3$^+$ T cells in the composition can be ascertained using the methodology described herein. Preferably, at least 75%, 85%, 90%, 95%, or 98% of said cells of the composition are FoxP3$^+$ T cells.

The cells may be administered for therapeutic purposes in any physiologically acceptable medium, normally intravascularly, although they may also be introduced into bone or other convenient site, where the cells may find an appropriate site for activation and differentiation. Usually, at least $1 \times 10^5$ cells will be administered, preferably $1 \times 10^6$ or more. The cells may be introduced by injection, catheter, or the like. The cells may be frozen at liquid nitrogen temperatures and stored for long periods of time, being capable of use on thawing. If frozen, the cells will usually be stored in a 10% DMSO, 50% FCS, 40% RPMI 1640 medium. Once thawed, the cells may be expanded by use of growth factors and/or stromal cells associated with progenitor cell proliferation and differentiation.

Another aspect of the invention is reagents and kits thereof for practicing one or more of the above-described methods. The subject reagents and kits thereof may vary greatly. In certain embodiments, the kits include at least an antibody to at least one of latency-associated peptide (LAP), IL-1 receptor type I (CD121a), IL-1 receptor type II (CD121b) and GARP (LRRC32). In other embodiments, the kit also includes at least one antibody specific for a T cell marker, e.g. CD4, CD8, CD3, etc. The antibody may be labeled or the kit may provide reagents for labeling the antibody. In addition to the above components, the kits will further include instructions for practicing the isolation methods and/or treatment methods of the present invention. These instructions may be present in the kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

Another aspect of the invention is methods of treatment (prophylactic and/or therapeutic) for autoimmune disorders, chronic graft-versus-host disease (cGVHD) and transplant rejection using the isolated FOXP3$^+$ Tregs described herein.

As used herein, "treatment" refers to clinical intervention in an attempt to alter the natural course of the individual or cell being treated, and may be performed either for prophylaxis and/or during the course of clinical pathology. Desirable effects include preventing occurrence or recurrence of disease, alleviation of symptoms, diminishment of any direct or indirect pathological consequences of the disease, preventing metastasis, lowering the rate of disease progression, amelioration or palliation of the disease state, and remission or improved prognosis. Accordingly, a therapeutic benefit is not necessarily a cure for a particular disease or condition, but rather, preferably encompasses a result which most typically includes alleviation of the disease or condition, elimination of the disease or condition, reduction of a symptom associated with the disease or condition, prevention or alleviation of a secondary disease or condition resulting from the occurrence of a primary disease or condition (e.g., glaucoma secondary to type 1 diabetes), and/or prevention of the disease or condition.

A beneficial effect can easily be assessed by one of ordinary skill in the art and/or by a trained clinician who is treating the patient. The term, "disease" refers to any deviation from the normal health of a mammal and includes a state when disease symptoms are present, as well as conditions in which a deviation (e.g., infection, gene mutation, genetic defect, etc.) has occurred, but symptoms are not yet manifested.

According to the present invention, the methods and assays disclosed herein are suitable for use in or with regard to an individual that is a member of the Vertebrate class, Mammalia, including, without limitation, primates, livestock and domestic pets (e.g., a companion animal). Most typically, a patient will be a human patient. According to the present invention, the terms "patient," "individual" and "subject" can be used interchangeably, and do not necessarily refer to an animal or person who is ill or sick (i.e., the terms can reference a healthy individual or an individual who is not experiencing any symptoms of a disease or condition).

Diseases and disorders that are characterized by altered (relative to a subject not suffering from the disease or disorder) regulatory T cell activity are treated with compositions, including pharmaceutical compositions or medicaments containing the FOXP3$^+$ Tregs described herein as a means of adoptive immunotherapy.

Accordingly, the methods of the present invention preferably modulate the activity of regulatory T cells, and specifically those that are naturally expressed by the cells of an individual (including an individual that has an autoimmune disease or condition). The method of the invention for example, involves contacting a cell, tissue or system of an individual with a composition containing the isolated FOXP3$^+$ Tregs of the present invention that modulates one or more of the activities of T cells in the individual. Such methods are preferably performed in vivo (e.g., by administering the agent to a subject). As such, the invention provides methods of treating an individual afflicted with a disease or disorder, specifically an autoimmune or transplant rejection disorder.

Autoimmune disorders that can be treated by the method of the invention include, but are not limited to, systemic lupus erythematosus (SLE), rheumatoid arthritis, type 1 diabetes, multiple sclerosis (MS), aplastic anemia, and idiopathic thrombocytopenic purpura. An effective amount of a composition containing FOXP3$^+$ Tregs to administer to an individual is any amount that achieves any detectable inhibition of the autoimmune disorder in the patient, or any detectable reduction in at least one symptom of the autoimmune disorder.

In the therapeutic methods of the invention, suitable methods of administering a composition of the present invention to a subject include any route of in vivo administration that is suitable for delivering the composition. The preferred route of administration is intravascularly, although they may also be introduced into bone or other convenient site, where the cells may find an appropriate site for activation and differentiation. The cells may be introduced by injection, catheter, or the like. Usually, at least $1 \times 10^5$ cells will be administered to the patient, preferably $1 \times 10^6$ or more.

The isolated FOXP3$^+$ Tregs generated ex vivo can be administered to a transplantation patient either before or after transplantation, preferably as a cell suspension in a suitable medium such as physiological saline. Intravenous administration, such as by intravenous infusion, is preferred although other modes of administration may be possible such as intraperitoneal administration or, in the case of certain types of transplant such as islet transplantation or skin transplantation, local administration at the graft site.

Administration of the FOXP3$^+$ Tregs a short time prior to transplantation, for example a day before, is preferred, which makes the present invention particularly suitable for use in the case of live donation of the organ or tissue transplant. Administration after initiation of the rejection process has commenced is unlikely to be effective but a protocol could be envisaged in which FOXP3$^+$ Tregs are administered at the optimal time point, i.e. shortly before transplantation, and FOXP3$^+$ Tregs are re-administered subsequently if clinical indicators suggest a decline in graft function. In this case it would be appropriate for Treg to be continuously stimulated/expanded by the method according to the invention for an appropriate period after transplantation as a contingency against delayed rejection.

The appropriate dose of FOXP3$^+$ Tregs will depend on the type of transplant and in the case of human recipients, will be at the discretion of the attendant physician. The precise numbers of ex vivo generated FOXP3$^+$ Tregs required to influence transplant rejection in humans will be determined by clinical trials but animal data suggests that doses in the range of $10^9$ to $10^{12}$ FOXP3$^+$ Tregs may be appropriate.

The recipient may be treated with additional immunosuppression or adjunctive therapy to attenuate any immediate rejection response that occurs. The additional immunosuppression or adjunctive therapy may comprise administration of a sub-therapeutic dose of an immunosuppressive agent, preferably an agent used in a manner (time/dose) that does not block the function of the regulatory T cells, in the immediate post-operative period. Suitable immunosuppressive agents or adjunctive therapies include treatment with an anti-CD8 antibody or with rapamycin. The intention is that the combination of the ex vivo generated FOXP3$^+$ Tregs with a sub-therapeutic dose of an immunosuppressive agent would lead to the prolonged survival of fully allogeneic allografts, for example cardiac allografts, in fully immunocompetent recipients. A sub-therapeutic dose can be identified by reference to clinical studies identifying suitable therapeutic doses.

The invention now being generally described will be more readily understood by reference to the following examples, which are included merely for the purposes of illustration of certain aspects of the embodiments of the present invention. The examples are not intended to limit the invention, as one of skill in the art would recognize from the above teachings and the following examples that other techniques and methods can satisfy the claims and can be employed without departing from the scope of the claimed invention.

EXAMPLES

Example 1

Cell Purification and Reagents Used

Cell leukapheresis products containing approximately $5 \times 10^9$ cells were obtained from healthy adult donors by the Department of Transfusion Medicine at the National Institutes of Health (NIH). The acquisition of blood products was approved according to the policies of the NIH in accordance with the Declaration of Helsinki Peripheral blood mononuclear cells (PBMCs) were obtained from 5 to 10 mL blood from patients with primary Sjögren syndrome or SLE who participated in Institutional Review Board-approved protocols at the National Institute of Dental and Craniofacial Research and the National Institute of Arthritis and Musculoskeletal and Skin Diseases, NIH (Bethesda, Md.). Written informed consent was obtained from all patients in accordance with the Declaration of Helsinki PBMCs were prepared over Ficoll-Paque Plus gradient centrifugation (GE Healthcare, Little Chalfont, United Kingdom). For FACS, $CD4^+$ cells were enriched over the AutoMACS Pro Separator by positive selection with human $CD4^+$ microbeads (Miltenyi Biotec, Auburn, Calif.). The cells were labeled with CD4 FITC, CD25 PE, CD45RA PE-Cy5.5 (all Invitrogen, Carlsbad, Calif.) and CD127 Alexa Fluor 647 (BD Biosciences, San Jose, Calif.). The FACSVantage DiVa or FACSAria flow cytometer was used to sort Tregs by gating on the top 2% $CD25^{hi}$ and non-Tregs by gating on $CD4^+CD25^-CD127^+$ $CD45RA^+$ cells. For magnetic bead purification based on CD25, the Miltenyi $CD4^+CD25^+$ Regulatory T Cell Isolation Kit was used with a modified manufacturer's protocol. In brief, all $CD4^+$ cells were depleted over the AutoMACS Pro with a cocktail of biotin-conjugated mAbs against CD8, CD14, CD16, CD19, CD36, CD56, CD123, $TCR\gamma/\delta$, and CD235a. The unlabeled $CD4^+$ T cells were incubated with CD25 microbeads (5 µL/$10^7$ $CD4^+$) and positively selected over the AutoMACS Pro with Posseld2 program. For magnetic bead purification based on CD25 and CD127, the Miltenyi $CD4^+CD25^+CD127^{dim/-}$ Regulatory T Cell Isolation Kit was used with a similar protocol. For the one-step method of $CD25^+$ cell purification, total PBMCs were incubated with CD25 microbeads (2 µL/$10^7$ cells) for 20 minutes at 4° C. and positively selected over the AutoMACS Pro with Posseld2 program. For magnetic bead sorting of in vitro-expanded $LAP^+$, $CD121a^+$, or $CD121b^+$ cells, the cells were stained with either anti-$LAP^+$ PE or anti-CD121a PE followed by anti-PE microbeads or anti-CD121b biotin followed by anti-biotin microbeads (both Miltenyi Biotec) then positively selected over the AutoMACS Pro with Possels then repeated with Possel program.

Antibodies conjugated to PE were as follows: CD73, CD120b, CD127, CD134, CD137, CD278 (from BD Biosciences); CD39, CD101 (from eBioscience, San Diego, Calif.); and GITR (from Miltenyi Biotec). For staining of CD121a, CD121b, and LAP, anti-LAP PE or anti-CD121a PE (both R&D Systems, Minneapolis, Minn.) and anti-CD121b biotin followed by secondary staining with streptavidin PE or APC (BD Biosciences) were used. For intracellular staining of FOXP3, the cells were fixed and permeabilized with a Fixation/Permeabilization kit and stained with anti-FOXP3 mAb Alexa Fluor 488 or 647 clone 236A/E7 (eBioscience). All cells were cultured in complete media consisting of RPMI 1640 supplemented with 5% heat-inactivated autologous serum, penicillin (100 U/mL), streptomycin (100 µg/mL), 2 mM L-glutamine, 10 mM HEPES, 0.1 mM nonessential amino acids, 1 mM sodium pyruvate and 50 µM 2-mercaptoethanol.

Example 2

In Vitro Expansion

Bead-purified $CD4^+CD25^+$ T cells ($10 \times 10^6$) were stimulated with anti-CD3/CD28-conjugated Dynabeads Human Treg Expander (Invitrogen) at 4:1 ratio of cell-to-bead in complete media supplemented with 100 U/mL IL-2 (PeproTech, Rocky Hill, N.J.) in the absence or presence of 25 nM rapamycin. The cells were stimulated in 12-well culture plates at $2 \times 10^6$ cells/well in 2 mL media.

On day 5, the cells were transferred to 75-$cm^2$ culture flasks with additional fresh complete media and 100 U/mL IL-2. No additional rapamycin was added to the rapamycin cultures. The cultures were maintained at cell concentration of $10^6$/mL and split every 3 days with additional fresh IL-2 media. On day 12, the cells were washed and given fresh IL-2 media before restimulation with additional Dynabeads at 4:1 cell-to-bead ratio. After 48-hour stimulation, the cells were analyzed and purified based on the expression of LAP, CD121a, or CD121b.

For de novo induction of FOXP3, $CD4^+CD25^-CD127^+$ $CD45RA^+$ or $CD45RO^+$ T cells sorted by FACS were stimulated with anti-CD3/CD28-conjugated Dynabeads at a 4:1 cell-to-bead ratio in complete media with 100 U/mL IL-2 and 5 ng/mL TGFβ1. On day 3, the Dynabeads were removed, and the cells were rested in IL-2 media. On day 7, the cells were restimulated with Dynabeads.

Example 3

In Vitro Suppression Assay

Fresh allogeneic CD4+$CD25^-$ T cells (50,000) sorted by FACS were stimulated with 50 000 irradiated (40 Gy [4000 rad]) autologous CD3-depleted PBMCs and 0.25 µg/mL OKT3 alone or with various numbers of suppressor cells. The cells were cultured for 3 days in 96-well flat-bottom plates (Corning) and pulsed with 3H-TdR (1 µCi [0.037 MBq]/well) for the last 6 to 8 hours. In similar experiments, fresh allogeneic CD4+$CD25^-$ T cells were labeled with 2 µM CFSE and stimulated with CD3-depleted PBMCs and 0.5 µg/mL OKT3 alone or with 4:1 and 8:1 responder to suppressor cells. The cells were cultured for 3 days, and CFSE dilution was analyzed by FACS.

Example 4

Flow Cytometric Analysis and Statistical Analysis

FACSCalibur was used for data acquisition, and the data were analyzed with FlowJo software (TreeStar, Ashland, Oreg.). For analysis of intracellular cytokine production, the cells were stimulated for 5 hours with 50 ng/mL PMA and 1 µg/mL ionomycin along with 3 µg/mL brefeldin A (eBioscience). Afterward, the cells were fixed and permeabilized with eBioscience kit and stained with anti-FOXP3 Alexa Fluor 647, anti-IFNγ Alexa Fluor 488, and anti-IL-2 PE.

All group results are expressed as mean plus or minus SD, if not stated otherwise. The paired Student t test was used for the comparison of group values and discriminatory parameters, where appropriate. P values less than 0.05 were considered significant.

Example 5

Magnetic Bead Purification of Human CD4$^+$CD25$^+$ CD127$^{low}$FOXP3$^+$ Tregs Although expression of CD25 and Foxp3 are highly correlated in mouse CD4□ T cells, in humans only those CD4$^+$ T$^{hi}$ cells expressing high levels of CD25 are uniformly FOXP3$^+$. Stringent FACS of the top 2% to 4% CD4$^+$T$^{hi}$ cells remains the best method of obtaining a greater than 90% FOXP3$^+$ population of Tregs, but results in a yield of only 20% to 40% of the total FOXP3$^-$ Tregs as the remainder are hidden within the population expressing intermediate level of CD25 (CD25$^{int}$) consisting mainly of recently activated and memory FOXP3$^-$ T cells. A large panel of mAbs were tested that have been claimed to specifically recognize Tregs for their reactivity with freshly explanted human PBMCs to determine whether any correlation could be detected between FOXP3 expression and their target antigens (FIG. 1, A). As has been previously reported only expression of low levels of CD127 appeared to correlate with FOXP3 expression. Expression of CD39, CD73, CD101, GITR, CD134 (OX40), CD137 (4-1BB), CD278 (ICOS), or CD120b (TNF RII) failed to consistently correlate with FOXP3 expression only.

Low levels of expression of CD127 alone are not helpful for isolating Tregs, but selection of cells expressing low levels of CD127 in combination with CD25 does result in a higher yield of FOXP3$^+$ T cells because it captures some of the CD4+CD25$^{int}$FOXP3$^+$ Tregs. Although CD127 depletion followed by CD25 bead purification resulted in a higher percentage of FOXP3$^+$ T cells (mean, 81%; range, 70%-90%; n=10) than purification with CD25 beads alone (mean, 76%; range, 63%-90%; n=10), the purity achieved by FACS of CD4$^+$CD25$^{hi}$ cells (mean, 94%; range, 90%-98%; n=20) was always significantly greater (FIGS. 1, C and D).

Example 6

In Vitro Expansion of CD$^{127}$lowCD25$^+$ Tregs Results in the Outgrowth of CD4$^+$FOXP3$^-$ T Cells and CD4$^+$FOXP3$^+$ Non-Tregs Cardinal features of FOXP3$^+$ Tregs are their nonresponsiveness to TCR stimulation and their requirement for exogenous cytokines, in particular IL-2, to proliferate. Therefore, in vitro expansion of Tregs necessitates strong CD3/CD28 stimulation in the presence of high concentration of IL-2. Under these conditions, the suppressive effects of the Tregs are masked, and any contaminating CD4$^+$CD25$^+$FOXP3$^-$ cells are likely to overgrow the culture. Using a leukapheresis product containing approximately 5×10$^9$ cells from healthy donors followed by Ficoll gradient separation of mononuclear cells, all non-CD4$^+$ and CD127$^+$ cells were initially depleted with magnetic beads and then enriched for CD25$^+$ cells to achieve a final yield of 20 to 60×10$^6$ CD4$^+$CD25$^+$ T cells. Several reports have shown that FOXP3$^-$ T cells are more susceptible to rapamycin-induced apoptosis, whereas Tregs are more resistant because of their constitutive expression of pim 2, a serine/threonine kinase with antiapoptotic effects. Therefore, 10×10$^6$ of the CD25$^+$ population was stimulated with anti-CD3/CD28-conjugated beads and IL-2 in the absence or presence of rapamycin. Although there was a reduction of up to 50% in expansion of the CD25$^+$ T cells in the presence of rapamycin for the first week, on subsequent restimulation in the absence of rapamycin, the expansion was only 20% to 30% less (FIG. 2, A). However, there was a progressive reduction in FOXP3 purity in the expansion cultures from an average of 82% (range, 70%-90%) FOXP3$^+$ cells in the starting population to a mean of 67% (range, 50%-86%) on day 7, 60% (range, 45%-72%) on day 14, and 53% (range, 40%-67%) on day 21 (FIG. 2, B). In the presence of rapamycin, there was an enhancement in FOXP3 purity with an average of 81% (range, 73%-88%) on day 7, 71% (range, 55%-87%) on day 14, and 64% (range, 42%-84%) on day 21. Because not all activated FOXP3$^+$ T cells are Tregs based on their lack of anergic properties, we evaluated whether FOXP3$^+$ non-Tregs were present in the expansion cultures. Indeed, a significant percentage of IFN-γ- and IL-2-producing cells were present in both expansion cultures after 14 days (FIG. 2, C). Most of these cells expressed lower levels of FOXP3 than did the cytokine nonproducers.

Example 7

LAP, CD121a, and CD121b are Expressed on Activated FOXP3$^+$ Tregs but not on FOXP3$^-$ and FOXP3$^+$ Non-Tregs Although a combination of high levels of expression of CD25 and low levels of expression of CD127 facilitates the identification and isolation of freshly explanted Tregs, activation of CD4$^+$CD25$^{-/int}$FOXP3$^-$ T cells results in up-regulation of CD25 and down-regulation of CD127. It is therefore impossible to separate activated Tregs from activated non-Tregs based on differential expression of these surface markers. A panel of antibodies with purported specificity for FOXP3$^+$ Tregs were therefore tested for their ability to distinguish expanded FOXP3$^-$ T cells from activated FOXP3$^-$ T cells. None of the mAbs consistently differentiated FOXP3$^+$ T cells during the expansion cultures before or after restimulation. In some studies, CD278 (ICOS) and CD137 (4-1BB) appeared to be selectively expressed on activated Tregs, but this result was highly variable and was observed approximately 50% of the time. However, when the day 12- and day 19-expanded cells were restimulated for 48 hours and the staining was repeated, anti-LAP, anti-CD121a, and anti-CD121b specifically and consistently reacted with FOXP3$^+$ T cells and not the FOXP3$^-$ T cells (FIG. 3, A). Similar to expanded Tregs, LAP and CD121a can be detected within 12 hours and CD121b after 24 hours of stimulation on freshly isolated Tregs, and all 3 surface markers are expressed optimally between 24 and 48 hours (FIG. 3, B) and disappear within 48 to 72 hours after stimulation. LAP, CD121a, and CD121b were coexpressed on the activated Tregs, although approximately 10% to 20% remained negative (FIG. 3, C). LAP has been previously reported to be a Treg-specific marker, although there was no direct correlation to FOXP3. Our previous studies had identified LAP on FOXP3$^+$ Tregs that had been previously activated via their TCRs. CD121a and CD121b was selected because preliminary microarray studies had suggested that they were differentially expressed on activated Tregs but not TGFβ-induced FOXP3$^+$ T cells. The TGFβ-induced FOXP3$^+$ non-Tregs fail to express LAP, CD121a, or CD121b after primary stimulation and with subsequent restimulation (FIG. 3, D). Therefore, our result indicates that LAP, CD121a, and CD121b are uniquely expressed on activated FOXP3$^+$ Tregs and might represent thymic-derived and not peripheral-converted Tregs.

Example 8

Selective Expression of LAP, CD121a, or CD121b Allows for Separation of Tregs from Non-Tregs in Ex Vivo Expansion Cultures The identification of LAP, CD121a, and CD121b as specific markers of activated Tregs provides an opportunity to separate activated FOXP3+ and FOXP3− cytokine-producing non-Tregs from activated FOXP3+ non-cytokine-producing Tregs by FACS or magnetic bead purification. As previously shown, the average percentages of FOXP3+ Tregs in the absence or presence of rapamycin on day 14 and 21 after 48 hours of restimulation were 60% versus 71% and 53% versus 64%, respectively. At the same time, the average percentages of LAP+ cells in the absence or presence of rapamycin on day 14 and 21 were 50% (range, 38%-58%) versus 54% (range, 46%-63%) and 51% (range, 38%-62%) versus 59% (range, 33%-81%), respectively (FIG. 4, A). Using magnetic bead selection for LAP on day 14-expanded cultures, Tregs were purified to a level of greater than 90% FOXP3+ from both populations (FIGS. 4, B and C). The average cell yield was $138 \times 10^6$ in the absence and $132 \times 10^6$ Tregs in the presence of rapamycin, starting with $10 \times 10^6$ CD25+ cells (mean, 82% FOXP3+; range 70%-90%) on day 0 (FIG. 4, D). Similar results were obtained with CD121a and CD121b bead separation. The CD127 depletion, CD25 bead selection methods are presented to show that even using the current "gold standard" method of purifying a starting population of FOXP3+ Tregs, the outgrowth of FOXP3− T cells is a major issue after the expansion cultures. However, a previously published protocol involving a one-step method of purifying Tregs with just CD25 magnetic beads was also used. With this method, the starting population contains an average of 62% CD4+FOXP3+ T cells (range, 47%-86%) with the remainder being B cells and non-CD4/CD8 cells. During the 21-day expansion, there was not a dramatic decrease in FOXP3 purity because of the disappearance of these contaminating non-T cells and an expansion of CD4+FOXP3− T cells (FIG. 5, A). The Tregs from the expanded cultures can then be purified with anti-LAP to obtain results similar to what was achieved with the multiple antibody approach (FIG. 5, C through E). This procedure is more practical and feasible, because it would require the development of only one new GMP reagent: anti-LAP, anti-CD121a, or anti-CD121b.

Example 9

LAP+, CD121a+, and CD121b+ FOXP3+ T Cells are Fully Functional Tregs

Although it is possible to obtain a highly purified FOXP3+ population based on selection of LAP+, CD121a+, or CD121b+ cells after restimulation of the expanded CD25+ cells or CD127$^{low}$CD25+ T cells, it is critical to show that the purified population is functional and represents a superior potential product for immunotherapy than the unseparated population. The capacity of LAP+, CD121a+, and CD121b+ Tregs purified from day 14 and 21 expansion cultures to suppress the proliferative responses of CD4+CD25− T cells in both 3H-TdR uptake and CFSE dilution assays was evaluated. LAP+ and CD121b+ Tregs purified from CD127$^{low}$CD25+ cells expanded in the absence or presence of rapamycin were more potent suppressors than was the unseparated expanded Treg population in both assays (FIG. 6). The LAP+ and CD121b− populations showed minimal suppressive activity. Similarly, LAP+, CD121a+, and CD121b+ Tregs purified from single-step CD25+ cells on day 21 of expansion were highly suppressive and superior to the unseparated population (FIGS. 7, A and D). Because LAP represents the surface membrane TGFβ complex, we assessed whether the LAP+ Tregs mediate their suppression via TGFβ. No data indicated that suppression was abrogated in the presence of high concentrations of neutralizing anti-TGFβ mAb (50 μg/mL) or recombinant LAP (5 μg/mL) or with siRNA knockdown of TGFβ1 that prevented LAP expression. Even starting with a Treg population of greater than 90% FOXP3 positivity after FACS on CD4+CD127−CD25$^{hi}$, there is typically a progressive loss of FOXP3 purity in the expansion cultures either secondary to the outgrowth of the few contaminating non-Tregs or a down-regulation of FOXP3. It is conceivable that there exists some peripherally converted, noncommitted FOXP3+ T cells that would lose their FOXP3 and revert back to effector T cells during the expansion cultures. Therefore, we evaluated whether continued expansion of the purified LAP+, CD121a+, and CD121b+ Tregs increases their cell numbers while maintaining their purity and phenotype. The Tregs purified from the expansion cultures after 14 or 21 days could be further expanded to increase their cell yield while maintaining their FOXP3 purity (FIG. 7, A and B, FIG. 8A). The expanded Tregs continue to retain their surface phenotype (CD25+, CD127−, CD27+, CD62L+) and suppressive functions (FIGS. 7, C and E, FIG. 8C). In addition to their suppressive function, FOXP3+ Tregs are characterized by their nonresponsiveness to TCR stimulation in vitro. The LAP+, CD121a+, and CD121b+ populations were also completely nonresponsive when cultured alone, whereas the LAP−, CD121a−, and CD121b− populations showed substantial proliferative responses. A more quantitative assay for the anergic state of Tregs is the measurement of cytokine production on a per cell basis by intracellular staining. After 14 days of expansion, the cultures were stimulated for 5 hours with PMA and ionomycin. Low percentages of IL-2-, TNF-α-, IFN-γ-, and IL-17-producing cells were detected in the FOXP3− population, and higher percentages were found in the FOXP3− population, but no significant IL-4 or IL-10 producers were detected (FIG. 9, A). After purification with anti-LAP, the majority of the IL-2-, IFN-γ-, and IL-17-producing cells could be readily detected in both the FOXP3$^{low}$LAP− and FOXP3− LAP− populations, and few could be detected in the LAP+ population. Analysis of the cytokine profiles at other time points, including day 7 and day 21 of the expansion cultures, produced similar results. Taken together, these functional studies confirm that, compared with the unseparated population of expanded CD4+CD25+CD127$^{low}$ or CD25+ cells, the purified LAP+, CD121a+, and CD121b+FOXP3+ populations are a relatively pure population of Tregs. All 3 populations appear to be similar in phenotype and function so that there does not seem to be an advantage in any of the 3 markers for purification.

Example 10

Application of Method to Obtain Sufficient Treg Number and Purity from Small Blood Samples of Patients A major obstacle in studying Tregs from patients, particularly the pediatric population, is the difficulty of obtaining sufficient Treg numbers and purity for functional and genomic analysis. For these reasons, most human studies evaluating Tregs are restricted to surface phenotyping. To overcome these limitations, we evaluated whether the expansion and repurification methods of the present invention can be used to isolate sufficient numbers of Tregs at high purity when starting with a sample of 5 to 10 mL blood from adults. CD25+ cells were isolated with magnetic beads from patients with Sjögren syndrome or SLE and expanded in vitro for 14 days. Typically, approximately 1 to $2 \times 10^6$ CD25+ cells are obtained from 5 to 10 mL blood to achieve a 25- to 50-fold expansion after 14 days of culture. Consistent with normal healthy donors, there were selective expression of LAP, CD121a, and CD121b on the FOXP3+ cells after 48 hours of restimulation of the expanded populations (FIGS. 10, A and B). Using anti-LAP magnetic bead purification, the Tregs were reisolated from the expansion cultures with greater than 90% FOXP3 purity and a cell yield ranging from 10 to 25×10$^6$ cells. LAP+ Tregs from patients with Sjögren syndrome or SLE were anergic and suppressive (FIGS. 10, C and D). The application of this technique should facilitate the detailed analysis of Tregs from patients with diseases in which Treg function may be abnormal.

Example 11

GARP or LRRC32 is Selectively Expressed on Activated FOXP3+ Tregs

Consistent with a previous publication (Wang R, Wan Q, Kozhaya L, Fujii H, Unutmaz D, Identification of a regulatory T cell specific cell surface molecule that mediates suppressive signals and induces Foxp3 expression, *PLoS ONE* 3:e2705, (2008)), we found that GARP mRNA is selectively expressed in fresh human Tregs and rapidly up-regulated after activation of CD4+CD25$^{hi}$ Tregs with anti-CD3/CD28 and IL-2 (FIG. 11, A). Only very low levels of mRNA were detected in CD4+CD25− T cells after activation for 5 days. While the addition of TGF-β1 resulted in the induction of FOXP3 mRNA in CD4+CD25− T cells, the level of GARP mRNA was not dramatically increased. Cell surface expression of either LAP or GARP was not significantly detected on freshly isolated Tregs (CD25$^{hi}$), but the expression of both LAP and GARP was rapidly up-regulated after activation (FIG. 11, B). GARP and LAP occasionally could be detected on <5% of activated CD4+CD127+CD25− T cells (FIG. 12, A). However, when we activated the CD4+CD25$^{int}$ population, which contains mostly CD45RO+FOXP3− T cells and some FOXP3+ Tregs, the vast majority of LAP and GARP could be detected on FOXP3+ Tregs. The rapid appearance and disappearance of LAP+/GARP+FOXP3− T cells during the 36 h of activation of CD25$^{hi}$ and CD25$^{int}$ most likely represent Tregs that have down-regulated their FOXP3 and could be on their way to cell death. Platelets also coexpressed LAP and GARP on their membranes (FIG. 11, C). In contrast to previous reports (Gandhi R, Anderson D E, Weiner H L, Cutting edge: Immature Human Dendritic Cells Express Latency-associated Peptide and Inhibit T cell Activation in a TGF-beta dependent manner, J. Immunol. 178:4017-21 (2007)), we were unable to detect any significant surface expression of LAP or GARP on plasmacytoid or myeloid DCs from peripheral blood (FIG. 11, D). Interestingly, the cell surface expression of both LAP and GARP requires the Golgi apparatus, since the addition of monensin or brefeldin A during the activation culture prevented their surface expression (FIG. 11, E).

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. A method of making an isolated population of FOXP3+ regulatory T cells, comprising
    obtaining a biological sample containing T-cells from a mammal;
    contacting the biological sample with a labeled antibody or antibody fragment that specifically recognizes a cell surface protein selected from the group consisting of IL-1 receptor type I (CD121a), IL-1 receptor type II (CD121b) and GARP (LRRC32) to identify FOXP3+ T cells that bind to the labeled antibody or antibody fragment; and,
    separating the cells that bind to the labeled antibody or antibody fragment from the biological sample to produce an isolated population of FOXP3+ regulatory T cells.

2. The method of claim 1, wherein the antibody label is at least one of biotin, avidin, streptavidin, fluorochromes, including phycobiliproteins, including phycoerythrin and allophycocyanins, fluorescein and Texas red.

3. The method of claim 1, wherein the antibody label is attached to the antibody by a linker which can be cleaved or separated or subject to hydrolysis by contact with an enzyme under physiological conditions.

4. The method of claim 1, wherein the separating further comprises sorting the T cells according to the amount of labeled antibody or antibody fragment bound to them, wherein cells having bound antibody are identified as FOXP3+ regulatory T cells and isolated from cells lacking antibody bound to them.

5. The method of claim 1, wherein the separating comprises an immunological selection technique selected from the group consisting of flow cytometry, fluorescence-activated cell sorting (FACS), and magnetic bead based isolation technique.

6. The method of claim 4, wherein the sorting is magnetic selection conducted using an antibody or antibody fragment conjugated to a magnetic particle.

7. The method of claim 1, wherein the isolated population of FOXP3+ regulatory T cells are greater than 70% FOXP3+ cells.

8. The method of claim 1, wherein the isolated population of FOXP3+ regulatory T cells are highly anergic.

9. The method of claim 1, wherein the isolated population of FOXP3+ regulatory T cells are nonresponsive to T cell receptor (TCR) stimulation in vitro.

10. The method of claim 1, wherein the isolated population of FOXP3+ regulatory T cells are immunosuppressive in vivo.

11. The method of claim 1, wherein the biological sample is selected from peripheral blood, spleen blood and cord blood.

12. The method of claim 1, wherein the biological sample comprises lymph node tissue.

13. The method of claim 1, further comprising contacting the biological sample, or a portion thereof, with a chemical that induces the expansion, proliferation, activation, or growth of T cells, or specific populations of T cells, prior to contacting the biological sample with a labeled antibody or antibody fragment.

14. The method of claim 1, wherein the biological sample or a portion thereof is contacted with a cell that induces the expansion, proliferation, activation, or growth of T cells or specific populations of T cells, prior to contacting the biological sample with a labeled antibody or antibody fragment.

15. The method of claim 14, wherein the cell is a stromal cell.

16. The method of claim 14, wherein the cell is one of a donor-specific antigen presenting cell, and an antigen presenting cell from a source separate from the donor.

17. The method of claim 1, further comprising suspending the isolated population of FOXP3+ regulatory T cells in a physiologically-acceptable medium.

* * * * *